United States Patent [19]

Kodama et al.

[11] 4,230,719

[45] Oct. 28, 1980

[54] NOVEL 2-[4-(3-METHYL-2-THIENYL)PHENYL]PROPIONIC ACID AND PHARMACEUTICALLY ACCEPTABLE SALT THEREOF AND METHOD FOR TREATING SYMPTOMS OF INFLAMMATION AND PAIN

[75] Inventors: Tsutomu Kodama, Toyama; Masao Nakabayashi, Namerikawa; Isao Watanabe, Toyama; Hiroshi Hirano, Oyabe; Norio Abe, Toyama; Katsufumi Tanaka, Toyama; Hirotoshi Arai, Toyama, all of Japan

[73] Assignee: Toyama Chemical Co., Ltd., Tokyo, Japan

[21] Appl. No.: 71,486

[22] Filed: Aug. 31, 1979

Related U.S. Application Data

[63] Continuation-in-part of Ser. No. 961,557, Nov. 17, 1978, abandoned.

[30] Foreign Application Priority Data

Nov. 21, 1977 [JP] Japan .............................. 52-138943

May 10, 1979 [JP] Japan .............................. 54-56331

[51] Int. Cl.$^3$ .................... C07D 333/24; A01K 31/38
[52] U.S. Cl. ...................................... 424/275; 549/79
[58] Field of Search .......................... 549/79; 424/275

[56] References Cited

FOREIGN PATENT DOCUMENTS 1119334  7/1968 United Kingdom ..................... 549/79

*Primary Examiner*—Robert Gerstl
*Attorney, Agent, or Firm*—Oblon, Fisher, Spivak, McClelland & Maier

[57] ABSTRACT

A novel 2-[4-(3-methyl-2-thienyl)phenyl]propionic acid and a pharmaceutically acceptable salt thereof. These compounds are useful for treating symptoms of inflammation and pain in mammals including man. This disclosure relates to such compounds, a process for producing the same, a pharmaceutical composition containing such a compound and a method for treating symptoms of inflammation and pain.

7 Claims, No Drawings

NOVEL 2-[4-(3-METHYL-2-THIENYL)PHENYL]PROPIONIC ACID AND PHARMACEUTICALLY ACCEPTABLE SALT THEREOF AND METHOD FOR TREATING SYMPTOMS OF INFLAMMATION AND PAIN

CROSS-REFERENCES TO RELATED APPLICATIONS

This application is a continuation-in-part of application Ser. No. 961,557 filed Nov. 17, 1978 now abandoned.

This invention relates to a novel 2-[4-(3-methyl-2-thienyl)phenyl]propionic acid represented by the formula [I],

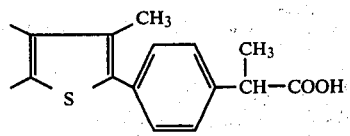

[I]

and a pharmaceutically acceptable salt thereof. This invention also relates to a process for producing such compounds, to a pharmaceutical composition containing such a compound, and to a method for treating symptoms of inflammation and pain.

Many non-steroidal anti-inflammatory analgesics have heretofore been proposed. These drugs, however, have either of the disadvantages of insufficiency in basic actions such as anti-inflammatory, analgesic, antirheumatic, and antipyretic activities; high toxicity, strong side effects such as ulcerogenic action or the like and undesirable effects of repeated administration. An undesirable tendency of the drugs in the prior art is that those drugs which are of high basic activities have a high toxicity and strong side effects, whereas those drugs which have a low toxicity and little side effect are unsatisfactory in basic activities. There exists a strong demand for the development of an anti-inflammatory analgesic having such a selective action that the basic activities against inflammation and pain are high while the toxicity is low and side effects are weak, permitting especially repeated administration. To meet the demand, research on novel drugs are now being conducted.

Under the circumstances, the present inventors have conducted extensive studies to develop a pharmaceutical preparation having a desirable selective action and advantages of high basic activities, low toxicity, weak side effect, and, in particular, practicability of repeated administration. As a result, it has been found that the compounds represented by the formula [I] and pharmaceutically acceptable salts thereof possess characteristic properties far superior to those of the representatives of conventionally known analgesic anti-inflammatory drugs and are able to achieve the above-mentioned objects.

2-[(2-Thienyl)phenyl]propionic acids are disclosed and known in British Pat. No. 1,119,334 and the compounds of this invention fall within the disclosure range of the said British patent specification, but are not specifically disclosed nor suggested therein. Therefore, the compounds of this invention are novel. The disclosure of the said British patent is vague, compounds specifically disclosed nor suggested therein are few, and neither physical properties nor pharmacological data of individual compounds have been given. The present inventors have synthesized typical analogous compounds falling within the scope of the British patent and compared them with the compound of this invention with respect to main activities, toxicity and side effects. Consequently, it has been found that the typical analogous compounds falling within the scope of the British patent have more undesirable properties than those of the representatives of conventionally known anti-inflammatory analgesics, whereas the compound of this invention has characteristics entirely different from and superior to those of not only the conventional antiinflammatory analgesics but also the analogous compounds of the British patent, and that said excellent characteristics of the compound of this invention originate from the methyl substituent at the 3-position of the thiophene ring.

It is an object of this invention to provide a novel compound which is useful as a therapeutic drug for the relief of inflammation and pain in mammals including man.

It is another object of this invention to provide a novel compound which is useful as a therapeutic drug for the relief of inflammation and pain caused by rheumatism.

It is a further object of this invention to provide a novel process for producing a compound represented by the formula [I] and a pharmaceutically acceptable salt thereof.

It is a still further object of this invention to provide a pharmaceutical composition containing a novel compound as active ingredient.

It is a still further object of this invention to provide a method for treating symptoms of inflammation and pain.

Other objects and advantages of this invention will become apparent from the following description.

The pharmaceutically acceptable salts of the compound of formula [I] of this invention include those which are known in this field. Examples thereof are salts with alkali metals such as sodium, potassium and the like; salts with alkaline earth metals such as calcium, magnesium and the like; salts with aluminum; and salts with various basic amino acids such as D-, L- and DL-lysines, D-, L- and DL-hydroxylysines, D-, L- and DL-arginines, D-, L- and DL-ornithines and the like.

The compound of formula [I] of this invention has optical isomers and racemic compound, all of which are included in the scope of this invention. The d-isomer has preferable properties.

An explanation is made below of various activities and properties of the present compound of formula [I], such as anti-inflammatory activity, anti-rheumatic activity, analgesic activity, toxicity, ulcerogenic action, inhibitory action on prostaglandin biosynthesis, action on glomerulonephritis in rat, uricosuric action, and antipyretic action in comparison with various analogous compounds and representatives of known anti-inflammatory analgesics.

(1) Tests for anti-inflammatory and anti-rheumatic activites.

(i) Vascular permeability in mice (Whittle's method)

The test compound was orally administered to each ddY strain male mouse (weighing each about 20 g). After 20 minutes, 0.1 ml/10 g of a 4%(Wt/V) solution of Pontamine Sky Blue in physiological saline was intravenously injected and 10 minutes thereafter 0.1 ml/10 g of a 0.7%(V/V) solution of acetic acid in physiological saline was injected intraperitoneally. After 30 minutes, the mice were killed by suffocation with chloroform. After immediate laparotomy, the dye leaked into the peritoneal cavity was washed out with distilled water. The washings were made up with water to 30 ml and the absorbance at 620 mμ was measured. The amount of leaked dye per 20 g of mouse weight was compared. The results obtained were as shown in Table 1.

TABLE 1

| Compound | Dosage (mg/kg p.o.) | Numer of animals (n) | Dye leakage (P.S.B.) (μg/20g) mean ± S.E. | Inhibition (%) | $ED_{30}$ (mg/kg p.o.) |
|---|---|---|---|---|---|
| Control | — | 18 | 320.8 ± 14.1 | — | — |
|  | 5 | 9 | 256.4 ± 15.9 | 20.1 |  |
| d-Isomer | 10 | 9 | 218.0 ± 14.3 | 32.0 | 8.6 |
|  | 20 | 9 | 160.4 ± 10.3 | 50.0 |  |
| [I] Racemic | 5 | 9 | 262.0 ± 21.1 | 18.3 |  |
| compound | 10 | 9 | 211.0 ± 26.0 | 34.2 | 8.5 |
|  | 20 | 9 | 166.8 ± 13.8 | 48.0 |  |
|  | 10 | 9 | 316.9 ± 29.0 | 18.0 |  |
| $C_1$ | 20 | 9 | 245.9 ± 15.4 | 36.4 | 16.0 |
|  | 5 | 9 | 314.7 ± 31.3 | 1.9 |  |
| $C_2$ | 10 | 9 | 264.8 ± 21.8 | 17.5 | 19.8 |
|  | 5 | 10 | 289.3 ± 21.4 | 9.8 |  |
| $C_3$ | 10 | 10 | 254.2 ± 10.3 | 20.8 | 20.5 |
|  | 20 | 9 | 226.9 ± 15.3 | 29.3 |  |
|  | 5 | 10 | 303.4 ± 13.3 | 5.4 |  |
| Diclofenac | 10 | 9 | 227.0 ± 14.4 | 29.2 | 14.0 |
| sodium | 20 | 11 | 205.3 ± 10.1 | 36.0 |  |
|  | 5 | 10 | 240.5 ± 25.9 | 25.0 |  |
| Indomethacin | 10 | 10 | 204.5 ± 17.6 | 36.3 | 6.8 |
|  | 20 | 10 | 176.4 ± 17.0 | 45.0 |  |

Note:

[I] = 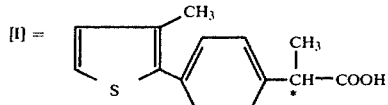

The compound of this invention. d-Isomer is an optical isomer at the asterisked carbon atom and racemic compound is an optically unresolved compound.

$C_1$ = 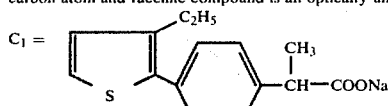

Included but not specifically mentioned in B.P. 1,119,334; a homolog of the compound [I] of this invention.

$C_2$ = 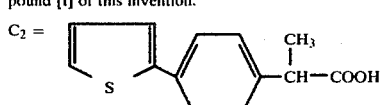

Included but not specifically mentioned in B.P. 1,119,334.

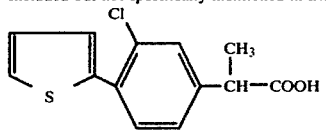

There is an Example of this compound in B.P. 1,119,334, but physical properites thereof are not stated.
Diclofenac sodium

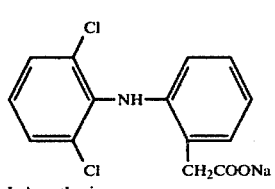

Indomethacin

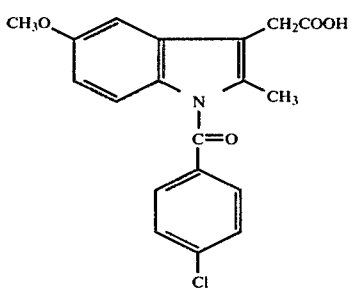

(ii) Vascular permeability in rat (Whittle's method)

The test compound was orally administered to each Wistar strain male rat (weighing about 150 g) which had been fasted overnight. After 55 minutes, 0.5 ml of a 0.5% Evans Blue solution was intravenously injected. Five minutes thereafter, 0.2 ml/100 g of a 3%(V/V) acetic acid solution was intraperitoneally injected. After 60 minutes from the injection of the acetic acid solution, the rats were killed by suffocation with chloroform. After immediate laparotomy, the dye leaked into the peritoneal cavity was washed out with physiological saline. The washings were made up with the saline to 30 ml and the absorbance at 640 mμ was measured to examine the effect of the test compounds by comparing the amounts of leaked dye per rat with one another. The results obtained were as shown in Table 2.

TABLE 2

| Compound | | Dosage (mg/kg p.o.) | Inhibition (%) | ED30 (mg/kg p.o.) |
|---|---|---|---|---|
| [I] | d-Isomer | 0.2 | 14.2 | 0.52 |
| | | 0.5 | 28.1 | |
| | | 1 | 43.3 | |
| | Racemic compound | 0.5 | 20.1 | 1.1 |
| | | 1 | 27.6 | 1.1 |
| | | 5 | 50.1 | |
| C2 | | 1 | 16.4 | 2.1 |
| | | 5 | 47.3 | |
| C3 | | 1 | 22.2 | 1.7 |
| | | 5 | 44.6 | |
| Diclofenac sodium | | 1 | 5.4 | 4.8 |
| | | 5 | 30.2 | |
| Indomethacin | | 0.5 | 20.7 | 1.0 |
| | | 1 | 32.5 | |
| | | 5 | 47.7 | |

(iii) Carrageenin-induced edema

Each of the 6 Donryu strain male rats per group (each weighing about 140 g), which had been fasted overnight, was orally loaded with 4 ml of water and, after 30 minutes, the test compound was orally administered thereto. Thirty minutes thereafter, a 1%(Wt/V) solution of carrageenin in physiological saline was subcutaneously injected into the subplantar region of the left hind paw. At a time interval of one hour, starting from the end of the first hour till the end of the fifth hour after injection of carrageenin, the paw volume was measured by means of a manometer and pressure transducer. By comparison with the percent increase in swelling of the control group of rats to which a 0.5%(V/V) solution of Tween 80 had been administered, the mean inhibitory percent in 5 hours of swelling was calculated by the following equation:

$$\text{Inhibitory percent of swelling (\%)} = \left(1 - \frac{\text{Swelling percent of the group to which test compound has been administered}}{\text{Swelling percent of the control group}}\right) \times 100$$

The results obtained were as shown in Table 3.

TABLE 3

| Compound | | Dosage (mg/kg p.o.) | Number of animals | Inhibitory percent of swelling(%) |
|---|---|---|---|---|
| [I] | d-Isomer | 1 | 6 | 40.0 |
| | | 5 | 6 | 57.2 |
| | Racemic compound | 1 | 6 | 21.2 |
| | | 5 | 6 | 48.5 |
| C1 | | 5 | 6 | 9.3 |
| C2 | | 1 | 6 | 11.8 |
| | | 5 | 6 | 32.9 |
| C3 | | 1 | 6 | 15.2 |
| | | 5 | 6 | 42.0 |
| C4 | | 5 | 6 | (−7.2) |
| | | 15 | 6 | (−2.7) |
| C5 | | 3 | 6 | −25.7 |
| | | 10 | 6 | 0.7 |
| C6 | | 5 | 6 | 19.1 |
| | | 15 | 6 | 31.4 |
| C7 | | 5 | 6 | −21.6 |
| | | 15 | 6 | 15.1 |
| C8 | | 5 | 6 | 17.0 |
| | | 15 | 6 | 41.9 |

TABLE 3-continued

| Compound | Dosage (mg/kg p.o.) | Number of animals | Inhibitory percent of swelling(%) |
|---|---|---|---|
| C9 | 5 | 6 | 15.1 |
| | 15 | 6 | 24.1 |
| Diclofenac sodium | 1 | 6 | 6.4 |
| | 5 | 6 | 39.8 |
| Indomethacin | 1 | 6 | 6.4 |
| | 5 | 6 | 46.2 |

Note:

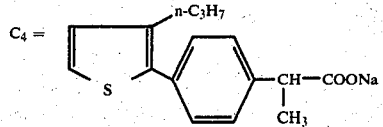

$C_4 =$

Included but not specifically mentioned in B.P. 1,119,334; a homolog of the compound [I] of this invention.

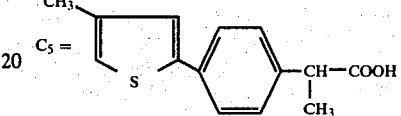

$C_5 =$

Included but not specifically mentioned in B.P. 1,119,334.

$C_6 =$

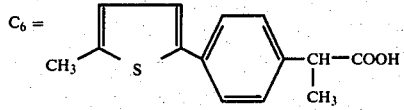

Included but not specifically mentioned in B.P. 1,119,334.

$C_7 =$

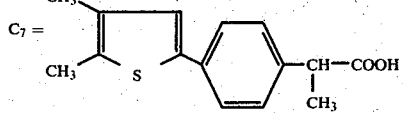

Included but not specifically mentioned in B.P. 1,119,334.

$C_8 =$

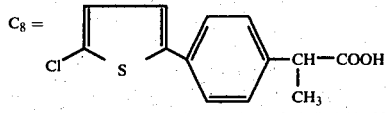

Included but not specifically mentioned in B.P. 1,119,334.

$C_9 =$

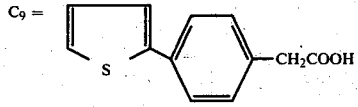

Included but not specifically mentioned in B.P. 1,119,334. This compound is an acetic acid derivative, whereas the compound of the formula [I] of this invention is a propionic acid derivative.

(iv) Adjuvant arthritis

A suspension containing 6 mg/ml of killed and dried Mycobacterium butyricum in liquid paraffin was subcutaneously injected into the subplantar region of the left hind paw of Sprague-Dawley strain male rats (weighing 180 to 200 g) in a proportion of 0.1 ml/rat. After 14 days, the rats having inflammatory paws of similar volumes were selected and the test compound was orally administered to the rats repeatedly at the rate shown in Table 4 during one week and the mean inhibitory percent of swelling during one week was determined. The results obtained were as shown in Table 4.

TABLE 4

| Compound | | Dosage (mg/kg p.o./day) | Number of animals (n) | Inhibitory percent of swelling (%) |
|---|---|---|---|---|
| [I] | d-Isomer | 1 | 6 | 21.6 |
| | Racemic compound | 1 | 6 | 14.4 |

TABLE 4-continued

| Compound | Dosage (mg/kg p.o./day) | Number of animals (n) | Inhibitory percent of swelling (%) |
|---|---|---|---|
| $C_2$ | 1 | 6 | 7.2 |
| $C_3$ | 1 | 6 | 8.1 |
| Diclofenac sodium | 1 | 6 | 10.9 |

(2) Test for analgesic activity (i) Phenylbenzoquinone method in mouse

The test compound was orally administered to each ddY strain male mouse (weighing 22±2 g; 8 mice per group). After 30 minutes, a 0.02% solution of phenylbenzoquinone in 24% aqueous polyethylene glycol solution was injected intraperitoneally at a rate of 0.1 ml/10 g. The frequency of writhing during 10 minutes from 5-minutes after the injection of phenylbenzoquinone was measured and compared with that of a control group to which a 0.5% Tween 80 solution was administered. The percent inhibition was calculated by the following equation:

$$\text{Percent inhibition} = \left(1 - \frac{\text{Frequency of writhing of the group to which test compound was administered}}{\text{Frequency of writhing of the control group}}\right) \times 100$$

The results obtained were as shown in Table 5.

TABLE 5

| Compound | | Dosage (mg/kg p.o.) | Frequency of writhing, mean ± S.E. | Inhibition (%) | $ED_{50}$ (mg/kg p.o.) |
|---|---|---|---|---|---|
| Control | | — | 23.6 ± 1.9 | — | — |
| [I] | d-Isomer | 5 | 14.5 ± 3.5 | 38.6 | 7.5 |
| | | 10 | 9.9 ± 2.6 | 58.1 | |
| | | 20 | 5.4 ± 1.0 | 77.1 | |
| | Racemic compound | 5 | 18.6 ± 4.5 | 21.2 | 9.7 |
| | | 10 | 11.8 ± 2.4 | 50.0 | |
| | | 20 | 3.3 ± 0.9 | 86.0 | |
| $C_1$ | | 10 | 23.6 ± 5.0 | 0 | >>50.0 |
| | | 20 | 23.7 ± 4.4 | −0.4 | |
| | | 40 | 23.1 ± 3.9 | 2.1 | |
| $C_2$ | | 10 | 22.3 ± 1.9 | 5.5 | 33.0 |
| | | 20 | 14.6 ± 3.1 | 38.1 | |
| | | 40 | 11.1 ± 2.4 | 53.0 | |
| $C_3$ | | 10 | 23.1 ± 3.5 | 2.1 | 50.0 |
| | | 20 | 19.4 ± 3.7 | 17.8 | |
| | | 40 | 12.4 ± 3.0 | 47.5 | |
| $C_4$ | | 40 | 24.0 ± 2.6 | −1.7 | >>50.0 |
| $C_5$ | | 40 | 23.4 ± 1.9 | 0.8 | >>50.0 |
| $C_6$ | | 40 | 18.2 ± 2.8 | 22.9 | >50.0 |
| $C_7$ | | 40 | 19.1 ± 3.8 | 19.1 | >50.0 |
| $C_8$ | | 20 | 17.5 ± 4.2 | 25.8 | 27.0 |
| | | 40 | 6.3 ± 0.6 | 73.3 | |
| $C_9$ | | 40 | 13.9 ± 1.6 | 41.1 | >40 |
| Diclofenac sodium | | 5 | 21.4 ± 3.0 | 9.3 | 17.7 |
| | | 10 | 16.2 ± 3.1 | 31.4 | |
| | | 20 | 10.9 ± 1.7 | 53.8 | |
| Indomethacin | | 5 | 13.8 ± 2.9 | 41.5 | 7.0 |
| | | 10 | 9.1 ± 3.1 | 61.4 | |
| | | 20 | 5.4 ± 2.1 | 77.1 | |

(ii) Randall-Selitto method in rat

A 10% dried brewer's yeast suspension was subcutaneously injected to the plantar region of right hind paw of Wistar strain male rats (70 to 100 g in weight) at a rate of 0.1 ml/rat. After one hour, the test compound was orally administered. One hour thereafter, the pain threshold value was measured four times at a time interval of one hour. The mean value of four values obtained was taken as the pain threshold value of each group of rats. The activity of the drug was assumed to be 100% when the pain threshold value was raised by 150 g. The results obtained were as shown in Table 6.

TABLE 6

| Compound | | Dosage (mg/kg p.o.) | Inhibition (%) | $ED_{50}$ (mg/kg p.o.) |
|---|---|---|---|---|
| [I] | d-Isomer | 1 | 37.1 | 4.4 |
| | | 5 | 48.5 | |
| | | 25 | 72.9 | |
| | Racemic compound | 1 | 44.3 | 6.1 |
| | | 5 | 45.2 | |
| | | 25 | 66.9 | |
| $C_2$ | | 1 | 33.8 | 14.5 |
| | | 5 | 35.2 | |
| | | 25 | 58.5 | |
| $C_3$ | | 1 | 14.4 | 16.5 |
| | | 5 | 32.5 | |
| | | 25 | 56.6 | |
| Diclofenac sodium | | 1 | 22.7 | 5.3 |
| | | 5 | 49.7 | |
| | | 25 | 74.9 | |
| Indomethacin | | 1 | 27.4 | 6.3 |
| | | 5 | 41.6 | |
| | | 25 | 75.6 | |

(iii) Analgesic action in chronic pain model of mouse

A 10% dried brewer's yeast suspension was subcutaneously injected into the tail of ddY strain male mice at a rate of 0.1 ml/mouse. On 6th or 7th injection, the tail was pressed at a constant speed to determine the threshold value of pain due to pressure stimuli. The test compound was orally administered and after 20, 40, 60, 90, 120 and 160 minutes the threshold value was measured. The activity of the test compound was determined from the maximum threshold value of the 6 values obtained, by taking the pain threshold as 100% when it was raised by 160 g from the value before the administration of the compound. The results obtained were as shown in Table 7.

TABLE 7

| Compound | | Dosage (mg/kg p.o.) | Number of animals (n) | Analgesic effect (%) | $ED_{50}$ mg/kg (p.o.) |
|---|---|---|---|---|---|
| [I] | d-Isomer | 2.5 | 10 | 38 | 5.2 |
| | | 10 | 10 | 61 | |
| | | 40 | 10 | 80 | |
| | Racemic compound | 2.5 | 10 | 33 | 7.0 |
| | | 10 | 10 | 50 | |
| | | 40 | 10 | 85 | |
| Diclofenac sodium | | 5 | 10 | 31 | 9.5 |
| | | 20 | 15 | 71 | |
| Indomethacin | | 5 | 10 | 44 | 6.0 |
| | | 20 | 10 | 80 | |
| Ketoprofen | | 10 | 10 | 40 | 19.5 |
| | | 40 | 10 | 61 | |
| Phenylbutazone | | 25 | 10 | 26 | 53.0 |
| | | 100 | 10 | 70 | |
| Ibuprofen | | 20 | 10 | 36 | 44.5 |
| | | 80 | 10 | 60 | |
| | | 200 | 10 | 25 | 710 |

TABLE 7-continued

| Compound | Dosage (mg/kg) p.o. | Number of animals (n) | Analgesic effect (%) | ED$_{50}$ mg/kg (p.o.) |
|---|---|---|---|---|
| Aspirin | 800 | 10 | 53 | |

Note:

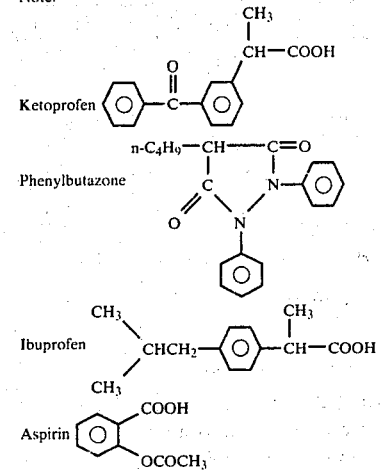

(3) Toxicity test

(i) Acute oral toxicity

The acute oral toxicity (LD$_{50}$) was examined by using Wistar strain male rats (each weighing 160 to 170 g). The results were as shown in Table 8.

TABLE 8

| Compound | LD$_{50}$ (mg/kg p.o.) |
|---|---|
| d-Isomer [I] | 230 |
| Racemic compound | 248 |
| C$_1$ | >400 |
| C$_2$ | 115 |
| C$_3$ | 270 |
| Diclofenac sodium | 103 |
| Indomethacin | 16.2 |

(ii) Test for the effect of repeated administration

To each group of Wistar strain male rats (each weighing about 200 g; 8 rats per group) was orally administered 20 mg/kg (except for 5 mg/kg in the case of Indomethacin) of the compound [I], C$_1$, C$_2$ or C$_3$, Diclofenac sodium, Indomethacin, or 0.5% Tween 80 repeatedly for one week. All the rats of the groups to which Diclofenac sodium and Indomethacin had been administered died. Although all the rats of the group to which the compound C$_2$ had been administered showed, though survived, slight disturbance of growth, as compared with the group to which 0.5% Tween 80 had been administered. The group to which the compound [I], C$_1$ or C$_3$ had been administered showed neither death case nor growth disturbance.

(4) Test for ulcerogenic action (i) The test compound suspended in 0.5% Tween 80 was orally administered at a rate of 1 ml/100 g to each Sprague-Dawley strain male rat (weighing about 180 g; 7 rats per group) which had been fasted for 48 hours. After 18 hours, the rats were killed by suffocation with chloroform and their stomachs were excised. After having been filled with 5 ml of 1% formalin to fix the gastric mucosa, each stomach was incised along the greater curvature to inspect grossly the extent of injury of the gastric mucosa. The extent of injury was scored as follows: 0, no lesion; 1, petechia or erosion; 2, 1–5 small ulcers; 3, many small ulcers; 4, many large ulcers or perforation. The intestinal injury was evaluated based on the incidence of erosion. The results obtained were as shown in Table 9.

TABLE 9

| Compound | Dosage (mg/kg) p.o. | Gastric glandular Score | UD$_{50}$ (mg/kg) p.o. | Intestine Erosion incidence |
|---|---|---|---|---|
| Control | — | 0.57 ± 0.13 | — | 0/7 |
|  | 10 | 0.92 ± 0.25 |  | 0/7 |
| d-Isomer | 30 | 1.62 ± 40.26 | 36 | 0/7 |
| [I] | 100 | 3.20 ± 0.32 |  | 2/7 |
|  | 10 | 0.86 ± 0.21 |  | 0/7 |
| Racemic | 30 | 1.36 ± 0.30 | 42 | 0/7 |
| compound | 100 | 3.07 ± 0.32 |  | 0/7 |
|  | 10 | 1.11 ± 0.21 |  | 1/7 |
| C$_2$ | 30 | 1.89 ± 0.24 | 25 | 1/7 |
|  | 100* | 3.61 ± 0.26 |  | 6/7 |
|  | 10 | 1.18 ± 0.30 |  | 0/7 |
| C$_3$ | 30 | 1.96 ± 0.42 | 27 | 0/7 |
|  | 100 | 3.39 ± 0.30 |  | 4/7 |
|  | 10 | 1.00 ± 0.31 |  | 0/7 |
| Diclofenac | 30 | 1.57 ± 0.43 | 28 | 0/7 |
| sodium | 100 | 3.79 ± 0.10 |  | 2/7 |
|  | 3 | 1.00 ± 0.27 |  | 0/7 |
| Indomethacin | 10 | 1.93 ± 0.40 | 7.8 | 0/7 |
|  | 30 | 3.93 ± 0.07 |  | 3/7 |

Note:
*Death incidence: 3/7

(ii) In the same manner as in (i), the test compound was orally administered to each Donryu strain male rat (weighing about 180 g; 10 rats per group) which had received normal meal. The second dose was administered after 8 hours and the third dose after 16 hours from the second dose. Five hours after the last administration, the rats were treated in the same manner as in (i). The gastric mucosa injury and the intestinal injury were scored in the same manner as in (i). The results obtained were as shown in Table 10.

TABLE 10

| Compound | Dosage (mg/kg × 3 p.o.) | Score Stomach | Mean ± S.E. Intestine |
|---|---|---|---|
| Control |  | 0.35 ± 0.08 | 0.40 ± 0.16 |
| [I] | 5 | 0.95 ± 0.22 | 0.40 ± 0.16 |
| (Racemic | 15 | 1.20 ± 0.13 | 0.50 ± 0.17 |
| compound) | 30 | 1.80 ± 0.29 | 2.90 ± 0.31 |
|  | 5 | 1.21 ± 0.18 | 1.07 ± 0.30 |
| C$_2$ | 15 | 2.33 ± 0.31 | 1.17 ± 0.21 |
|  | 5 | 1.67 ± 0.31 | 0.83 ± 0.21 |
| C$_3$ | 15 | 2.36 ± 0.14 | 1.50 ± 0.38 |
| Diclofenac | 5 | 0.90 ± 0.22 | 1.00 ± 0.21 |
| sodium | 15 | 1.15 ± 0.25 | 3.30 ± 0.26 |
|  | 5 | 1.95 ± 0.22 | 3.50 ± 0.22 |
| Indomethacin | 15 | 3.10 ± 0.23 | 3.90 ± 0.10 |

As is apparent from Tables 1 to 4, with respect to the anti-inflammatory and anti-rheumatic activities, the compound of this invention is comparable to commercially available Indomethacin, is superior to Diclofenac sodium and markedly superior to the reference compounds C$_1$ to C$_9$ falling within the scope of British Pat. No. 1,119,334. It is understandable from Tables 5 to 7 that with respect to the analgesic activity, the compound of this invention is comparable to Indomethacin, is superior to Diclofenac sodium, Ketoprofen, Phenylbutazone, Ibuprofen, Asprin and far superior to the reference compounds $C_1$ to $C_9$ falling within the scope of British Pat. No. 1,119,334. Further, it is seen from Table 8 and the results of test (3)-(ii) that as compared with the reference compound $C_2$, Diclofenac sodium and Indomethacin, the compound of this invention possesses a lower toxicity and is markedly different in the effect of repeated administration. As is apparent from Tables 9 and 10, the compound of this invention causes side effects more rarely than the reference compounds $C_2$ and $C_3$, Diclofenac sodium and Indomethacin.

As is apparent from the foregoing description, it is understandable that in the overall pharmacological effect the compound of this invention is markedly superior to Diclofenac sodium and Indomethacin, not to speak of the reference compounds $C_1$ to $C_9$ falling within the scope of British Pat. No. 1,119,334 In addition, as described above, the compound of this invention is entirely different in basic activities, toxicity and side effects from the reference compounds and possesses advantageous properties such as desirable selective action and tolerance for repeated administration. It is surprising that such characteristic properties are acquired solely by the introduction of a methyl substituent into the 3-position of the thiophene nucleus.

The superiority of the compound of this invention over conventional anti-inflammatory drugs is confirmed by taking into account collectively the results of tests for not only the aforementioned anti-inflammatory, anti-rheumatic and analgesic activities (vascular permeability in mice, vascular permeability in rats, carrageenin-induced edema, adjuvant arthritis, phenylbenzoquinone method in mouse, Randall-Selitto method in art, and analgesic action in chronic pain model mouse), but also other actions as an anti-inflammatory analgesic (inhibitory action on prostaglandin biosynthesis, action on glomerulonephritis in rats, uricosuric action, antipyretic action and the like), as described below. Thus, the compound of this invention has properties useful in anti-inflammatory, analgesic and anti-rheumatic agents.

(5) Other tests for an anti-inflammatory analgesic (i) Inhibitory action on prostaglandin biosynthesis Using a homogenate of guinea pig's lung as an enzyme preparation for the biosynthesis of prostaglandin, the inhibitory activity of the test compound against the prostaglandin biosynthesis was examined by the TBA (thiobarbituric acid) method. The results obtained were as shown in Table 11.

TABLE 11

| Compound | $ID_{50}$ ($\mu M$) |
|---|---|
| [I] d-Isomer | 1.1 |
| Racemic compound | 1.4 |
| Diclofenac sodium | 1.0 |
| Indomethacin | 5.7 |
| Phenylbutazone | 68 |

(ii) Action on glomerulonephritis in rats

Glomerulonephritis was induced in Wistar strain male rats (each weighing 180 to 200 g) by use of an anti-rat's kidney rabbit serum obtained from the serum of a rabbit sensitized with a homogenate of rat's kidney cortice. To the rat producing stable proteinuria was orally administered the test compound repeatedly at the rate shown in Table 12 for 2 weeks, and the inhibition of uric protein was examined. The results obtained were as shown in Table 12.

TABLE 12

| Compound | Dosage (mg/kg p.o./day) | Number of animals | Inhibition of uric protein (%) 7th day | Inhibition of uric protein (%) 14th day |
|---|---|---|---|---|
| [I] d-Isomer | 10 | 20 | 33.4 | 44.1 |
| Racemic compound | 10 | 20 | 22.9 | 35.0 |
| Indomethacin*[1] | 2 | 20 | 14.0 | 8.9 |
| Phenylbutazone*[1] | 25 | 20 | 1.0 | 11.2 |
| Hydrocortisone*[2] acetate | 10 | 10 | 20.0 | 29.0 |

Note:
*[1]Representatives of conventionally known effective analgesic anti-inflammatories. Diclofenac sodium showed a low activity.
*[2]A steroidal anti-inflammatory drug frequently used clinically.

(iii) Uricosuric action (a) The action was examined by the method of B. B. Brodie et al. who reported that the inhibitory action on Phenol Red (PSP) excretion correlates with the uricosuric action [Proc. Soc. Exp. Biol. Med., 86, 884 (1954)]. To a male rabbit weighing 2 to 3 kg was intraperitoneally administered the test compound. After 30 minutes, 75 mg/kg of a Phenol Red suspension was injected into the pinna vein of the rabbit and 30 minutes thereafter a blood sample was drawn from the pinna vein. The blood sample was centrifuged and the serum was diluted with physiological saline. The diluted serum was treated with 0.1 N NaOH to develop the color. The concentration of Phenol Red in the serum was determined from the absorbance at 560 m$\mu$. The results obtained were as shown in Table 13.

TABLE 13

| Compound | Dosage (mg/kg i.p.) | Number of animals | Concentration of PSP in serum ($\mu$g/ml) mean ± S.E. |
|---|---|---|---|
| Control | — | 3 | 91.7 ± 20.3 |
| [I] d-Isomer | 10 | 3 | 223.8 ± 3.9 |
|  | 20 | 3 | 267.3 ± 18.0 |
| Racemic compound | 10 | 3 | 166.7 ± 25.1 |
|  | 20 | 3 | 249.3 ± 41.4 |
| Phenylbutazone*[1] | 50 | 3 | 174.0 ± 5.0 |
|  | 100 | 3 | 238.0 ± 15.9 |

Note:
*[1]A representative of conventionally known effective anti-inflammatory analgesics.

Indomethacin is very weak in the uricosuric action.

(b) After fasting overnight, the test compound was orally administered to a Wistar strain male rat weighing 150 to 200 g. After one hour, the rat was loaded with 100 mg/kg of uric acid by intraperitoneal administration. Thirty minutes thereafter, a blood sample was drawn from the cervical vein and the uric acid concentration in the plasma was determined by use of a kit (Uric acid test Wako) for the uric acid determination. The results obtained were as shown in Table 14.

TABLE 14

| Compound | Dosage (mg/kg p.o.) | Number of animals (n) | Uric acid concentration in plasma (mg/dl) mean ± S.E. |
|---|---|---|---|
| Control | — | 10 | 5.4 ± 0.18 |

TABLE 14-continued

| Compound | Dosage (mg/kg p.o.) | Number of animals (n) | Uric acid concentration in plasma (mg/dl) mean ± S.E. |
|---|---|---|---|
| [I] (Racemic compound | 10 | 5 | 5.3 ± 0.26 |
| | 20 | 5 | 3.4 ± 0.24 |
| Phenyl- | 50 | 5 | 5.3 ± 0.37 |
| butazone | 100 | 6 | 3.3 ± 0.25 |

(iv) Antipyretic action

A suspension (0.6 mg/0.1 ml) of killed and dried *Mycobacterium butyricum* in liquid paraffin was subcutaneously injected in an amount of 0.1 ml into the subplantar region of the hind paw of each Wistar strain female rat weighing about 180 g. After 14 hours, the fevered rats were divided into groups, and each test compound was orally administered to each group to examine the antipyretic effect. The results obtained were as shown in Table 15.

TABLE 15

| Compound | Dosage (mg/kg p.o.) | Mean decrease in temp. (°C.) | $ED_{1.0}$ (mg/kg p.o.) |
|---|---|---|---|
| [I] d-Isomer | 0.2 | 0.82 | |
| | 1 | 1.18 | 0.44 |
| | 5 | 1.63 | |
| [I] Racemic compound | 0.2 | 0.52 | |
| | 1 | 1.20 | 0.66 |
| | 5 | 1.70 | |
| Diclofenac sodium | 0.2 | 0.88 | |
| | 1 | 1.63 | 0.25 |
| | 5 | 1.57 | |
| Indomethacin | 0.2 | 0.25 | |
| | 1 | 0.87 | 1.06 |
| | 5 | 1.35 | |
| Phenylbutazone | 5 | 0.27 | |
| | 20 | 1.10 | 26.5 |
| | 100 | 1.35 | |

As described in the foregoing, the compound of this invention possesses markedly superior activities, far beyond the self-evident bounds, over those of the analogous reference compounds falling within the scope of British Pat. No. 1,119,334. As compared even with typical known analgesic anti-inflammatory drugs, it is much better in activities and safety. Thus, the compound of this invention is very useful in treating inflammation, pain and rheumatism.

The effective dose and the mode of administration of the compound of this invention are described below.

The compound of the formula [I] of this invention or a pharmaceutically acceptable salts thereof is mixed with pharmaceutically acceptable carriers or diluents by a conventional method and administered orally or parenterally in the form of capsule, powder, granule, pill, tablet, suspension, emulsion, syrup, injection or suppository. The daily dose (administered once to three times a day) of the compound of formula [I] or a pharmaceutically acceptable salt thereof for the effective elimination of inflammation, pain or fever is generally 0.1 to 50 mg per kg of the body weight, though may be varied appropriately, depending on the symptom. Accordingly, it is convenient for use if one unit of the preparation contains 10 to 100 mg of the active ingredient. More particularly, in the case of a solid preparation such as powder, granule, capsule, pill or tablet, the active ingredient is preferably mixed with at least one diluent such as, for example, starches, lactose, sucrose, or the like, while granules, pills or tablets preferably contain, beside the diluent, a binder such as, for example, various starches in solution, methylcellulose, gelatin solution or crystalline cellulose and a disintegrator such as, for example, starches, agar, calcium carboxymethylcellulose, or the like. Tablets may contain a lubricant such as, for example, magnesium stearate, stearic acid, talc or the like. If necessary, tablets may be applied with enteric coatings. Suspensions, emulsions, syrups, injections and suppositories may be prepared in a customary manner.

Typical recipe examples are given below.

Recipe Example 1

| Ingredient | mg/tablet |
|---|---|
| 2-[4-(3-Methyl-2-thienyl)phenyl]- propionic acid | 25.0 |
| Lactose | 56.0 |
| Starch | 37.5 |
| Crystalline cellulose | 30.0 |
| Magnesium stearate | 1.5 |
| Tablet | 150.0 mg |

Recipe Example 2

| Ingredient | mg/tablet |
|---|---|
| 2-[4-(3-Methyl-2-thienyl)phenyl]- propionic acid | 25.0 |
| Lactose for granulation | 69.0 |
| Calcium celluloseglycolate | 5.0 |
| Magnesium stearate | 1.0 |
| Tablet | 100.0 mg |

The methods of preparing the compound of formula [I] are described below.

The compound of formula [I] of this invention can be prepared, for example, in a customary way from a compound of formula [IV] which is synthesized, according to the following scheme, from a p-aminobenzene derivative of formula [II] and 3-methylthiophene of formula [II] and 3-methylthiophene of formula [III] by utilizing the Gomberg-Bachmann-Hey reaction [J. Am. Chem. Soc., 48, 1372 (1926); "Organic Reaction", Vol. II, 224–261]. $R^1$ in the compound of formula [IV] can be transformed into other substituents in a customary way.

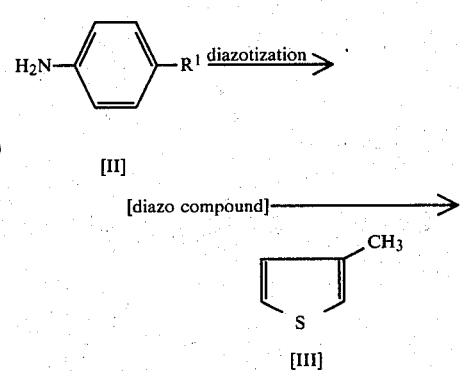

-continued
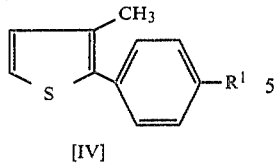
wherein $R^1$ represents —COCH$_3$, —COCH$_2$CH$_3$, —COOH, —COO(alkyl), —CN, —NO$_2$, a halogen atom, —CHO, —COCHO, —COCOOH or —COCOO(alkyl).
The compound of formula [II] can be obtained from the compound of formula [IV] in a known way according to the following scheme:
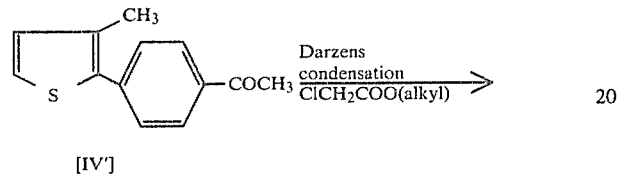
The compund of formula [1] can also be obtained by the methods of the following schemes:
-continued
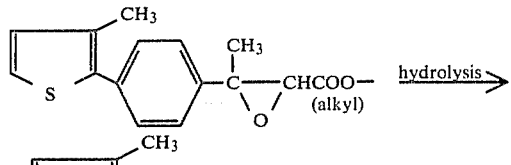
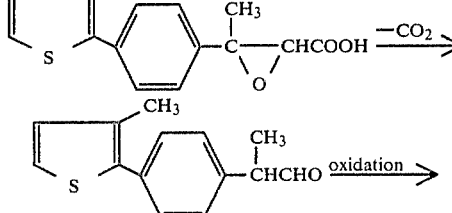
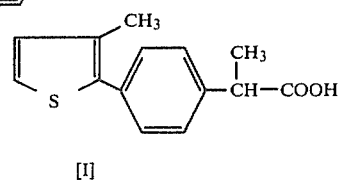
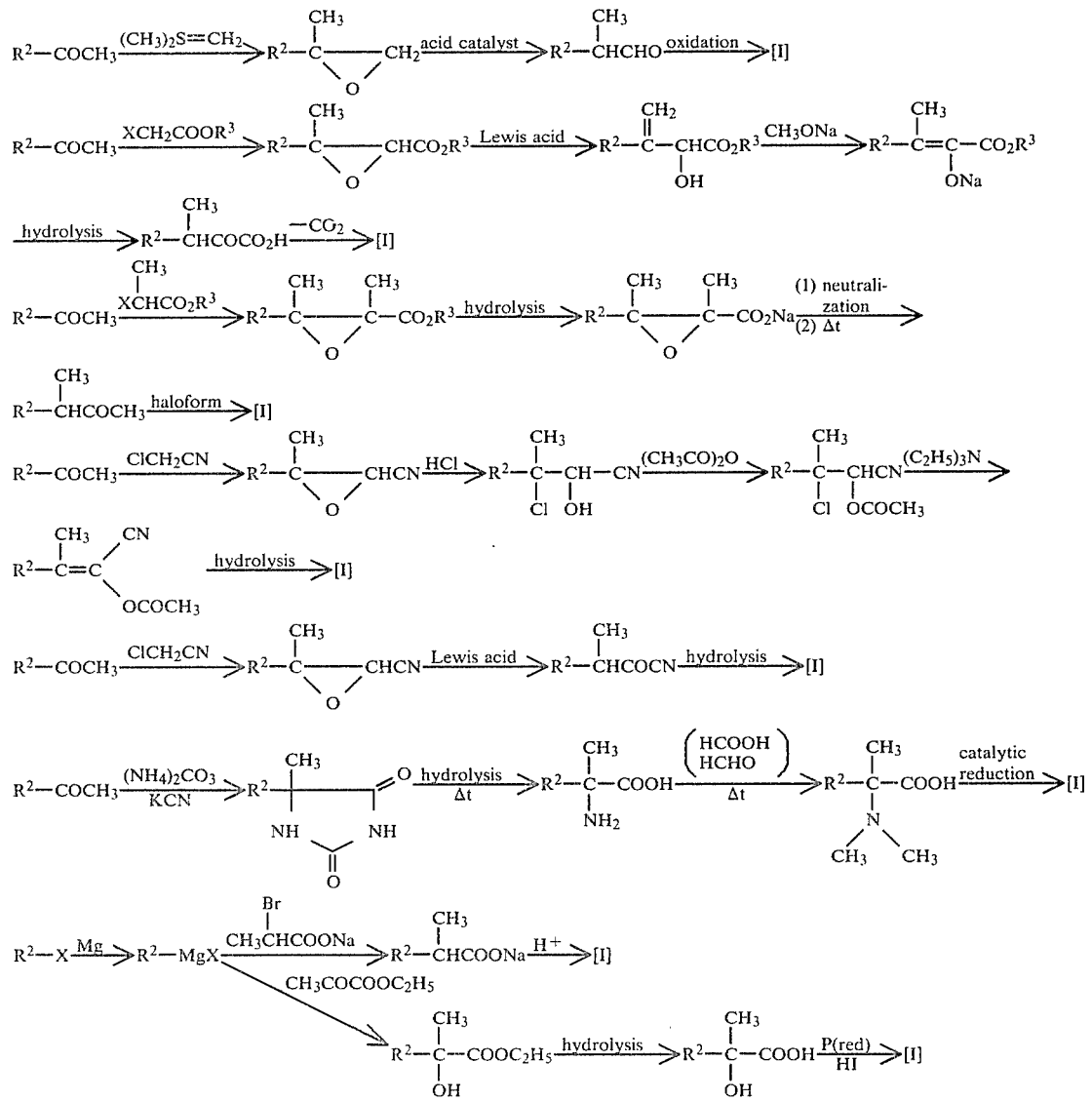

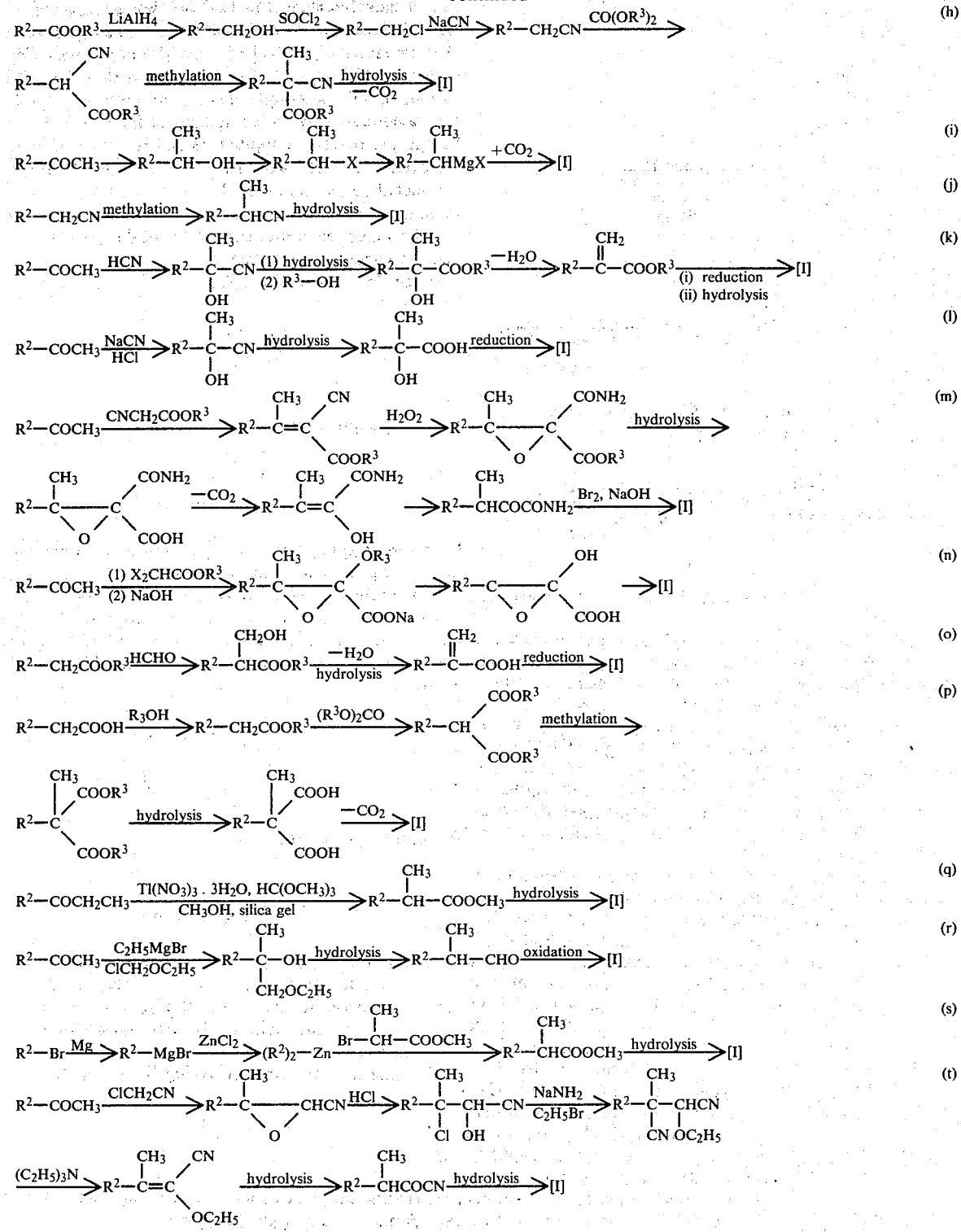
In the above formulas, $R^2$ represents
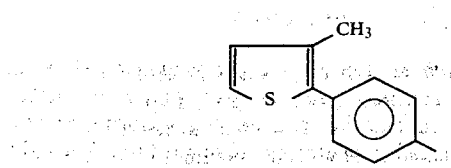
$R^3$ represents, for example, an alkyl group, and X represents a halogen atom.
The compound of formula [I] can also be synthesized according to the following novel reaction scheme:

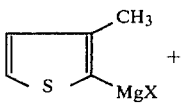

[V]

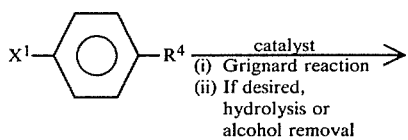

[VI]

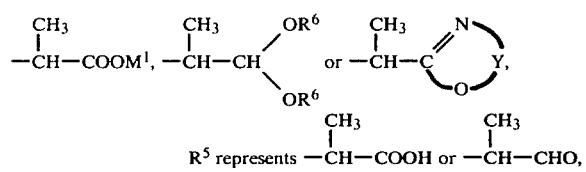

In the above formulas, X and X¹ represent the same or different halogen atoms, R⁴ represents

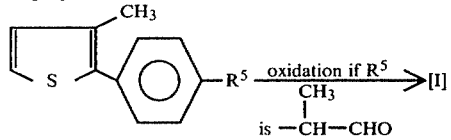

$R^5$ represents $-\overset{CH_3}{\underset{|}{CH}}-COOH$ or $-\overset{CH_3}{\underset{|}{CH}}-CHO$.

M¹ represents a metal atom, preferably an alkali metal, an alkaline earth metal, aluminum, tin, lead, antimony, bismuth, copper, nickel, cobalt, iron, manganese, chromium, titanium, cadmium, silver, zinc, or the like. R⁶ represents an alkyl group having preferably 1 to 5 carbon atoms or an alkenyl group having preferably 2 to 5 carbon atoms, or when two R⁶'s are taken together they may form a linear or branched alkylene group having preferably 2 to 4 carbon atoms and Y represents a linear or branched alkylene group having preferably 2 to 4 carbon atoms.

In practicing the above-noted Grignard reaction, the compound of formula [V] is reacted with the compound of formula [VI] in the presence of a catalyst in at least one solvent inert to the reaction such as tetrahydrofuran, dioxane, diethyl ether, benzene, toluene and the like. Suitable catalysts are inorganic palladium catalysts, such as palladium black, palladium carbon and palladium halides, for example, palladium chloride, palladium bromide or the like, or organic palladium, nickel or platinum catalysts of the formula, M²(PR⁷₃)₄, M²(PR⁷₃)₂(R⁸)X², M²(PR⁷₂—R⁹—PR⁷₂)X²₂ or M²(acac), wherein M² represents palladium, nickel or platinum; R⁷ and R⁸ represent lower alkyl groups, lower alkoxy groups, cycloalkyl groups or those phenyl, phenoxy, phenyl(lower)alkyl or phenyl(lower)alkoxy groups which may be optionally substituted by halogen, lower alkyl or the like; R⁹ represents C₁₋₁₀ alkylene groups or lower alkenylene groups; X represents a halogen atom; and acac is acetoacetonate. Said catalysts include palladium catalysts, for example, tetrakis(triphenylphosphine)palladium, iodo(phenyl)bis(triphenylphosphine)palladium, bromo(phenyl)bis(triphenylphosphine)palladium, tetrakis(triethylphosphine)palladium, iodo(p-fluorophenyl)bis(triphenylphosphine)palladium, tetrakis(tributylphosphine)palladium, tetrakis(tricyclohexylphosphine)palladium and dichloro[1,2-bis(diphenylphosphino)ethane]palladium, organic nickel catalysts, for example, tetrakis(triethylphosphine)nickel and nickel acetoacetonate, and organic platinum catalysts, for example, tetrakis(triethylphosphine)platinum. Of these catalysts, palladium catalysts are particularly preferred. The amount of the catalyst used is generally 0.01 to 0.0001 mole equivalent, preferably 0.001 mole equivalent based on the compound of formula [V]. Although the reaction temperature and reaction time are subject to no particular restriction, it is preferable to conduct the reaction at the refluxing temperature of a solvent for 30 minutes to several hours. It is preferred that the above reaction is effected in the anhydrous state under a nitrogen atmosphere.

When R⁴ in the formula [VI] is

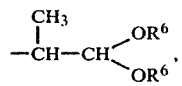

it is easily converted to

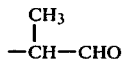

by the hydrolysis at room temperature or with heating in the presence of an acid catalyst such as, for example, hydrochloric acid, sulfuric acid, acetic acid, p-toluenesulfonic acid, trichloroacetic acid or phosphoric acid or alternatively by dealcoholization in the presence of acetic acid, oxalic acid, formic acid or the like. When R⁴ is

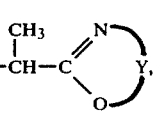

it is easily converted to

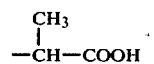

by hydrolysis at room temperature or under application of heat in the presence of an alkali catalyst such as an alkali hydroxide or an acid catalyst such as hydrochloric acid, sulfuric acid, p-toluenesulfonic acid or trichloroacetic acid.

The reaction product having the grouping

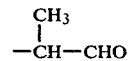

(R⁵) is easily converted in a customary way to the compound [I] having the grouping

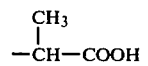

by oxidation with potassium permanganate, silver oxide, hydrogen peroxide, chlorous acid, hypochlorous acid, sodium chlorite, sodium hypochlorite or nitric acid in an alkaline, neutral or acidic medium. The oxidation is preferably carried out at a temperature exceeding 50° C. When the compound of formula [I] in which R⁴ is

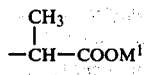

is used, the reaction product having the grouping

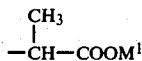

is easily converted in a customary way to the compound of formula [I] having the grouping

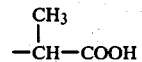

by using a mineral acid after the Grignard reaction. The compound of formula [I] thus formed is isolated and purified as usual. The starting materials [V] and [VI] are easily produced by a known method.

The above-mentioned route for producing the compound of formula [I] by Grignard reaction is a novel one and is excellent particularly in yield and purity of the product and in the ease of procedure, as compared, for example, with the method of Gomberg-Bachmann-Hey.

The compound represented by the formula [VI] may be optical isomers or a racemic compound, and there may be obtained optical isomers and racemic compound of the objective compound from the starting optical isomers and racemic compound, respectively.

When the objective compound obtained by the above-mentioned various methods is a racemic compound, optical isomers can be obtained by optical resolution of the racemic compound in the conventional manner. A preferable method for the optical resolution of a racemic compound to obtain a d-isomer which is an optical isomer is as follows: An optically active base such as optically active α-phenylethylamine, 1-phenyl-2-methylaminopropane, bornylamine, menthylamine, 2-amino-1-oxyhydrindene, α-cyclohexylethylamine, arginine, lysine, morphine, strychinine, brucine, quinine, quinidine, cinchonine, cinchonidine, ephedrin, and the like, or an ester or acid amide derived from α-phenylglycine, phenylalanine, leucine, tyrosine, valine, S-benzylcystine, proline, arginine, lysine or the like is allowed to act on a racemic acompound, thereby resolving a d-isomer in the form of a salt. The amount of the optically active base or the ester or acid amide is usually 0.4 to 0.6 mole per mole of the racemic compound. The solvent used in the resolution includes ethyl acetate, ethyl alcohol, methyl alcohol, propyl alcohol, butyl alcohol, acetone, water, benzene, toluene, xylene, chloroform, petroleum ether and the like, which are usually used. However, the solvent is not limited thereto, and there may be used any solvent which does not participate in the reaction. A mixture of them may be used, too. The resolution is usually effected at room temperature or elevated temperatures.

From the d-isomer salt obtained by the above-mentioned method, there can easily be obtained d-isomer by allowing such an acid as hydrochloric acid, sulfuric acid, phosphoric acid, acetic acid or the like, or such a base as sodium hydroxide, potassium hydroxide, calcium hydroxide or the like. Moreover, if necessary, a purified objective compound can be obtained by recrystallization.

An l-isomer which is also an optical isomer can also be obtained by optical resolution in a conventional manner.

According to a method disclosed in German Offenlegungsschrift No. 2,809,794, a d-isomer can be obtained from a racemic compound or an l-isomer. That is to say, the above-mentioned optically active base or ester or acid amide is added to the racemic compound or the l-isomer in an equimolar ratio, whereby a salt thereof is formed in a hydrocarbon solvent such as n-hexane, petroleum ether, ligroine, heptane, octane, nonane, decane, kerosene, (−)-α-pinene, myrcene, toluene or the like, after which the resulting mixture is heated under reflux, and then subjected to such operations as separation of the resulting d-isomer salt, purification and decomposition of the salt and the like, upon which the objective compound is obtained from the racemic compound or l-isomer in a good yield.

The compound of formula [I] can be converted in a conventional way to its pharmaceutically acceptable salts.

The methods for producing the starting materials and the compound of this invention are described below in detail with reference to Examples, which are merely illustrative and not limitative.

EXAMPLE 1

(1) Synthesis of 4-(3-methyl-2-thienyl)acetophenone

Method I: In a mixture of 30 ml of methanol, 30 ml of acetic acid and 150 g (1.53 moles) of 3-methylthiophene was dispersed 27 g (0.157 mole) of 4-aminoacetophenone hydrochloride, followed by the addition of 28 g (0.237 mole) of isoamyl nitrite. To the stirred mixture at room temperature was added portionwise 15 g (0.183 mole) of anhydrous sodium acetate, while cooling in water to maintain the temperature at 20° to 30° C. After completion of the addition, the mixture was stirred for 4 hours. The reaction mixture was freed from the solvent by distillation under reduced pressure and the residue was extracted with diisopropyl ether. The organic layer was washed with alkaline water, dried over anhydrous magnesium sulfate, then treated with activated carbon, and then freed from the solvent by distillation, and the residue was distilled under reduced pressure to obtain 20 g (58.8% yield) of 4-(3-methyl-2-thienyl)acetophenone, pale yellow in color.

Boiling point: 180°–182° C./6 mmHg.

I.R. (liquid film): $\nu_{C=O}$ 1665 cm$^{-1}$.

NMR(CDCl$_3$): 60 MHz, internal standard TMS τ value: 7.68 (s, CH$_3$ at 3-position of thiophene, 3H); 7.44 (s, —COCH$_3$, 3H); 3.16 (d, H at 4-position of thiophene, 1H, J=5 Hz); 2.83 (d, H at 5-position of thiophene, 1H, J=5 Hz); 2.55 (d, H at 3- and 5-positions of benzene, 2H, J=8 Hz); 2.11 (d, H at 2- and 6-positions of benzene, 2H, J=8 Hz)

Method II: To a mixture of 150 g (1.53 moles) of 3-methylthiophene and 50 ml of methanol, which had been cooled to −10° to 0° C., was added 43 g (0.183 moles) of 4-acetylbenzene diazonium tetrafluoroborate obtained from diazonium salt of 4-aminoacetophenone and 42% borofluoric acid. To the stirred mixture was added dropwise at −10° to 0° C. 70 ml of a methanol solution containing 9.9 g (0.183 mole) of powdered sodium methylate (95% purity), accompanied by vigorous evolution of nitrogen. After completion of the dropwise addition, the reaction mixture was gradually heated to room temperature, stirred at 20° to 30° C. for 3 hours, and then freed from the solvent and excess 3-methylthiophene by distillation under reduced pressure. The residue was extracted with diisopropyl ether while applying heat. The organic layer was washed with alkaline water, dehydrated with saturated aqueous sodium chloride solution, and freed from the solvent. The residue was treated in the same manner as in method I to obtain 21 g (53% yield) of 4-(3-methyl-2-thienyl)acetophenone.

Method III: To a mixture of 120 g (1.22 moles) of 3-methylthiophene and 40 g (0.296 mole) of 4-aminoacetophenone was added dropwise with stirring at 20° C. 41.5 g (0.355 mole) of isoamyl nitrite. After completion of the dropwise addition, the mixture was allowed to react under reflux for one hour and then freed from the excess 3-methylthiophene by atmospheric distillation. The residue was treated in the same manner as in the method I or II to obtain 23 g (36% yield) of 4-(3-methyl-2-thienyl)acetophenone.

(2) Synthesis of methyl 3-methyl-3-[4-(3-methyl-2-thienyl)phenyl]glycidate

In 150 ml of tetrahydrofuran was dissolved 20 g (0.0925 mole) of 4-(3-methyl-2-thienyl)acetophenone, followed by the addition of 20 g (0.184 mole) of methyl monochloroacetate to form a solution. To the resulting solution cooled to −5° to 0° C. was added gradually 10.5 g (0.185 mole) of sodium methylate (95% pure), while maintaining the temperature at −5° to 0° C. After completion of the addition, the mixture was stirred at the same temperature for one hour, then at room temperature for a further one hour, and finally refluxed for 30 minutes. After removal of the solvent by distillation under reduced pressure, the residue was admixed with 100 ml of diisopropyl ether and 50 ml of water. The organic layer was separated and filtered through a celite filter to remove a minute amount of insolubles. The filtrate was dried over anhydrous magnesium sulfate and freed from the solvent by distillation to obtain 25 g (92% yield) of almost pure methyl 3-methyl-3-[4-(3-methyl-2-thienyl)phenyl]glycidate in oily form.

I.R. (liquid film): $\nu_{C=O}$ 1750 cm$^{-1}$.

(3) Synthesis of 3-methyl-3-[4-(3-methyl-2-thienyl)phenyl]glycidic acid

To 100 ml of an ethanol solution containing 7.5 g (0.115 mole) of potassium hydroxide (85% pure) was added 30 g (0.104 mole) of methyl 3-methyl-3-[4-(3-methyl-2-thienyl)phenyl]glycidate. The mixture was refluxed for one hour. After removal of the ethanol by distillation, 200 ml of water was added to the mixture. In order to remove insolubles, 100 ml of benzene was added to the mixture, which was then thoroughly shaken. The separated aqueous layer was adjusted to pH 3 with 10% hydrochloric acid to liberate an oily substance which was extracted with diisopropyl ether. The organic layer was separated, dried over anhydrous magnesium sulfate and freed from the diisopropyl ether by distillation under reduced pressure to obtain 17 g (60% yield) of 3-methyl-3-[4-(3-methyl-2-thienyl)phenyl]glycidic acid.

I.R. (liquid film): $\nu_{C=O}$ 1720 cm$^{-1}$.

(4) Synthesis of 2-[4-(3-methyl-2-thienyl)phenyl]propionaldehyde

In 100 ml of toluene was dissolved 17 g (0.062 mole) of 3-methyl-3-[4-(3-methyl-2-thienyl)phenyl]glycidic acid and the solution was refluxed for one hour. After the evolution of carbon dioxide had ceased and the solution had been cooled, 100 ml of a 10% aqueous sodium hydrogencarbonate solution was added to wash the organic layer. The organic layer was dehydrated with saturated aqueous sodium chloride solution, then treated with activated carbon and freed from the solvent by distillation under reduced pressure. To the residue was added 100 ml of n-hexane and the mixture was heated under reflux to effect hot extraction. The insoluble matter separated from the n-hexane solution was extracted twice with 50-ml portions of n-hexane in the same manner as mentioned above. The extract solutions were collected and freed from the n-hexane by distillation to obtain 12 g (85% yield) of almost pure 2-[4-(3-methyl-2-thienyl)phenyl]propionaldehyde.

I.R. (liquid film): $\nu_{C=O}$ 1715 cm$^{-1}$.

(5) Synthesis of 2-[4-(3-methyl-2-thienyl)phenyl]propionic acid

In a mixed solvent of 90 ml of acetone and 30 ml of water was dissolved 9 g (0.0391 mole) of 2-[4-(3-methyl-2-thienyl)phenyl]propionaldehyde. To the solution cooled to −5° to 0° C. was added gradually with stirring 6.1 g (0.039 mole) of potassium permanganate, while maintaining the temperature within the same range. After completion of the addition, the solution was stirred for one hour at the same temperature. To the solution was then added dropwise 10 ml of a 30% aqueous hydrogen peroxide solution to destroy the excess permanganate. The reaction mixture was filtered through a celite filter to remove manganese dioxide and then freed from the acetone by heating. To the resulting concentrated solution was added 10 ml of 1 N sodium hydroxide solution, followed by extraction with diisopropyl ether. The aqueous layer, which was separated, was adjusted to pH 7.5 and filtered through a celite filter to remove a minute amount of insolubles. The filtrate was neutralized with 10% hydrochloric acid to adjust the filtrate to pH 5.5. The liberated oily substance was extracted with diisopropyl ether. The organic layer was dried over anhydrous magnesium sulfate, then treated with activated carbon and freed from the diisopropyl ether by distillation. The residue was crystallized by the addition of n-hexane to obtain 4.5 g (47% yield) of crude crystals of 2-[4-(3-methyl-2-thienyl)phenyl]propionic acid. When recrystallized from a n-hexane-cyclohexane mixture, the crystals showed a melting point of 96°–97° C.

I.R. (KBr): $\nu_{C=O}$ 1700 cm$^{-1}$.

NMR (CDCl$_3$): 60 MHz, interval standard TMS τ value:

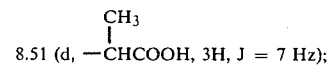
8.51 (d, —CHCOOH, 3H, J = 7 Hz);

7.75 (s, CH$_3$ at 3-position of thiophene, 3H);

6.29 (q, —CH—COOH, 1H, J = 7 Hz);

3.20 (d, H at 4-position of thiophene, 1H, J=5 Hz); 2.92 (d, H at 5-position of thiophene, 1H, J=5 Hz); 2.70 (s, H at 2-, 3-, 5- and 6-positions of benzene, 4H)

(6) To 19.5 ml of 1 N sodium hydroxide solution was added 4.9 g (0.02 mole) of 2-[4-(3-methyl-2-thienyl)-phenyl]propionic acid. After stirring for 30 minutes, the insoluble substance was removed by extraction with 20 ml of chloroform. The aqueous layer was concentrated under reduced pressure with heating. The residue was recrystallized from a toluene-water-dioxane mixture to obtain dihydrate of sodium 2-[4-(3-methyl-2-thienyl)-phenyl]propionate having melting point of 206°–207° C.

Determination of water by Karl Fischer's method:
  Found: 11.78%
  Theoretical: 11.84%

EXAMPLE 2

(1) Synthesis of methyl 2,3-dimethyl-3-[4-(3-methyl-2-thienyl)phenyl]glycidate

In 30 ml of tert.-butanol were dissolved 5.0 g (0.0232 mole) of 4-(3-methyl-2-thienyl)acetophenone and 8.5 g (0.0693 mole) of methyl α-chloropropionate. To the solution was added gradually at 20° to 30° C. 6.5 g (0.058 mole) of potassium tert.-butoxide. After completion of the addition, the mixture was stirred for one hour at room temperature and then for a further one hour under reflux. After completion of the reaction, the tert.-butanol was removed by distillation under reduced pressure. The residue was extracted by addition of 30 ml of cyclohexane and 30 ml of water. The cyclohexane extract solution was washed with water, dried over anhydrous magnesium sulfate, and freed from the cyclohexane by distillation under reduced pressure to obtain 7.1 g (100% yield) of almost pure methyl 2,3-dimethyl-3-[4-(3-methyl-2-thienyl)phenyl]glycidate in oily form.

I.R. (liquid film): $\nu_{C=O}$ 1730, 1750 cm$^{-1}$.

NMR (CDCl$_3$): 60 MHz, internal standard TMS cis-trans mixture τ value:

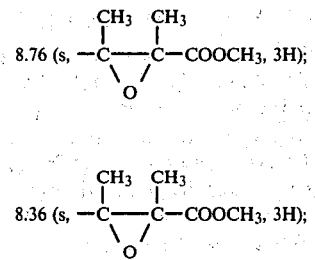

7.66 (s, CH$_3$ at 3-position of thiophene, 3H); 6.22 (s, —COOCH$_3$, 3H); 3.19 (d, H at 4-position of thiophene, 1H, J=5 Hz); 2.91 (d, H at 5-position of thiophene, 1H, J=5 Hz); 2.66 (s, H at 2-, 3-, 5- and 6-positions of benzene, 4H)

(2) Synthesis of 3-[4-(3-methyl-2-thienyl)phenyl]2-butanone

In 21 ml of ethanol was dissolved 7.1 g (0.0235 mole) of methyl 2,3-dimethyl-3-[4-(3-methyl-2-thienyl)-phenyl]glycidate obtained in (1). After addition of 1.7 g (0.0315 mole) of sodium methylate, the solution was stirred at room temperature, and then 0.5 ml of water was added thereto. The mixture was gradually heated and refluxed for 30 minutes. The reaction mixture was freed from the ethanol by distillation under reduced pressure and the residue was dispersed in 40 ml of xylene, after which 5 ml of acetic acid was added thereto. The mixture was heated under reflux for 4 hours. After completion of the reaction, the xylene layer was washed with water, then with 20 ml of 1 N sodium hydroxide solution, again with water, dried over anhydrous magnesium sulfate, and freed from the solvent by distillation under reduced pressure to obtain 4.3 g (76% yield) of 3-[4-(3-methyl-2-thienyl)phenyl]-2-butanone in oily form.

I.R. (liquid film): $\nu_{C=O}$ 1705 cm$^{-1}$.

NMR (CCl$_4$): 60 MHz, internal standard TMS τ value:

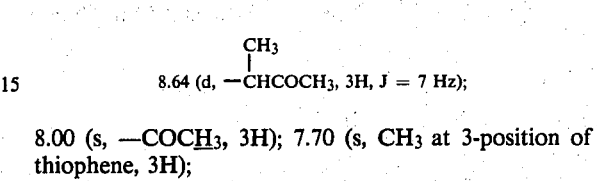

8.00 (s, —COC$\underline{H}_3$, 3H); 7.70 (s, CH$_3$ at 3-position of thiophene, 3H);

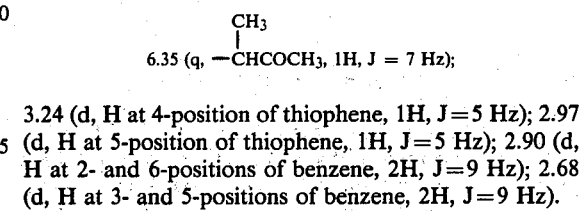

3.24 (d, H at 4-position of thiophene, 1H, J=5 Hz); 2.97 (d, H at 5-position of thiophene, 1H, J=5 Hz); 2.90 (d, H at 2- and 6-positions of benzene, 2H, J=9 Hz); 2.68 (d, H at 3- and 5-positions of benzene, 2H, J=9 Hz).

(3) Synthesis of 2-[4-(3-methyl-2-thienyl)phenyl]propionic acid

In 40 ml of dioxane was dissolved 4.3 g (0.0176 mole) of 3-[4-(3-methyl-2-thienyl)phenyl]-2-butanone obtained in (2). To the resulting solution was added dropwise at 30° to 40° C. 20 ml of a sodium hypobromite solution prepared from 9.1 g of bromine and 9.1 g of sodium hydroxide. The mixture was stirred at the said temperature for one hour. To the mixture were added 40 ml of water and 20 ml of chloroform to extract impurities. To the aqueous layer was added 20 ml of cyclohexane and the solution was adjusted to pH 3 with hydrochloric acid. The organic layer was dried over anhydrous magnesium sulfate and freed from the solvent by distillation under reduced pressure to obtain 3.0 g (76.2% yield) of 2-[4-(3-methyl-2-thienyl)phenyl]propionic acid in crystalline form. A sample obtained by recrystallization from cyclohexane and a sample of the product obtained in Example 1-(5) were subjected to the mixed melting point test. No depression in melting point was observed.

EXAMPLE 3

(1) Synthesis of 2-[4-(3-methyl-2-thienyl)phenyl]propionaldehyde

In 25 ml of acetonitrile was dissolved 5.0 g (0.0232 mole) of 4-(3-methyl-2-thienyl)acetophenone, followed by the addition of 8.7 g (0.046 mole) of trimethylsulfonium methyl sulfate. To the mixture was added with stirring at room temperature 2.5 g (0.0464 mole) of sodium methylate. After having been stirred for one hour, the mixture was freed from the solvent by distillation under reduced pressure. To the residue was added 20 ml of toluene, and the solution was washed several times with water, dried over anhydrous magnesium sulfate, and freed from the solvent by distillation under reduced pressure to obtain 5.2 g (97.4% yield) of almost pure oily 2-[4-(3-methyl-2-thienyl)phenyl]-2-methyloxirane. This oxirane compound was dissolved in 25 ml of toluene, admixed with 0.5 g of powdered Molecular Sieves 4A, and refluxed for one hour. The Molecular Sieves was removed by filtration and the filtrate was freed from the solvent by distillation under reduced pressure to obtain 5.1 g (98% yield) of oily 2-[4-(3-methyl-2-thienyl)phenyl]propionaldehyde.

I.R. (liquid film): $\nu_{C=O}$ 1715 cm$^{-1}$;

$\nu$CH   2705, 2805 cm$^{-1}$
(CHO)

NMR (CCl$_4$): 60 MHz, internal standard TMS $\tau$ value:

8.63 (d, —$\overset{CH_3}{\underset{|}{CH}}$—, 3H, J = 7 Hz);

7.77 (s, CH$_3$ at 3-position of thiophene, 3H);

6.46 (q, —$\overset{CH_3}{\underset{|}{CH}}$—, 1H, J = 7 Hz);

3.21 (d, H at 4-position of thiophene, 1H, J=5 Hz); 2.93 (d, H at 5-position of thiophene, 1H, J=5 Hz); 2.90 (d, H at 2- and 6-positions of benzene, 2H, J=8 Hz); 2.61 (d, H at 3- and 5-positions of benzene, 2H, J=8 Hz);

0.45 (d, —$\overset{CH_3}{\underset{|}{CH}}$CHO, 1H, J = 1Hz)

(2) Synthesis of 2-[4-(3-methyl-2-thienyl)phenyl]propionic acid

In 20 ml of water was dissolved 3.2 g (0.033 mole) of sulfamic acid. To the solution was added a solution of 5.0 g (0.0217 mole) of 2-[4-(3-methyl-2-thienyl)phenyl]propionaldehyde [obtained in (1)] in 20 ml of chloroform. To the mixture, while maintaining the temperature at 0° to 10° C., was added dropwise with stirring 10 ml of an aqueous solution containing 2.6 g (0.0242 mole) of sodium chlorite (84% pure). After completion of the addition, the mixture was stirred for 10 minutes, admixed with 2.6 g (0.025 mole) of sodium hydrogensulfite, further stirred for 30 minutes, and allowed to stand, upon which the mixture separated into two layers. The organic layer was washed with 20 ml of water and extracted by the addition of 25 ml of 1 N aqueous sodium hydroxide solution. To the alkaline extract layer, which had been admixed with 20 ml of cyclohexane, was added gradually with stirring 5% hydrochloric acid to adjust the pH to 4. The organic layer was washed with water, dried over anhydrous magnesium sulfate, and freed from the solvent by distillation under reduced pressure to obtain an oily substance which was crystallized by the addition of a small quantity of n-hexane to yield 4.8 g (90% yield) of 2-[4-(3-methyl-2-thienyl)phenyl]propionic acid.

EXAMPLE 4

(1) Synthesis of 5-[4-(3-methyl-2-thienyl)phenyl]5-methylhydantoin

In a mixture of 50 ml of ethanol and 34 ml of water was dissolved 5.0 g (0.0232 mole) of 4-(3-methyl-2-thienyl)acetophenone. After addition of 11 g of ammonium carbonate and 3.1 g of potassium cyanide, the mixture was allowed to react at 60° to 65° C. for 10 hours. After completion of the reaction, the ethanol was removed from the reaction mixture by distillation, to obtain a white solid substance. This solid substance was washed with water by dispersing it in water and filtering to obtain 6.1 g (96% yield) of 5-[4-(3-methyl-2-thienyl)phenyl]-5-methylhydantoin in crystalline form.

Melting point: 201°-202.5° C. (after recrystallization from ethyl acetate).

I.R. (KBr): $\nu_{NH}$ 3230, 3280 cm$^{-1}$. $\nu_{C=O}$ 1725, 1770 cm$^{-1}$.

(2) Synthesis of 2-amino-2-[4-(3-methyl-2-thienyl)phenyl]propionic acid

To a solution of 3.0 g of sodium hydroxide in 30 ml of water was added 5.0 g (0.0183 mole) of 5-[4-(3-methyl-2-thienyl)phenyl]-5-methylhydantoin obtained in (1). The mixture was subjected to hydrolysis by heating in a sealed tube at 170° C. for 4 hours. Upon cooling the reaction mixture after completion of the reaction, crystals were precipitated. The mixture was adjusted to pH 5 with hydrochloric acid and the crystals were collected by filtration and washed with water to obtain 4.4 g (92% yield) of 2-amino-2-[4-(3-methyl-2-thienyl)phenyl]propionic acid having a melting point of more than 250° C.

(3) Synthesis of 2-dimethylamino-2-[4-(3-methyl-2-thienyl)phenyl]propionic acid

To a mixture of 8 ml of formic acid and 5 ml of formalin (40%) was added 4.0 g (0.0153 mole) of 2-amino-2-[4-(3-methyl-2-thienyl)phenyl]propionic acid obtained in (2). After refluxing for one hour, the mixture was freed from the solvent by distillation under reduced pressure, to obtain a white solid substance which was then washed with acetone to obtain 3.6 g (81% yield) of 2-dimethylamino-2-[4-(3-methyl-2-thienyl)phenyl]propionic acid.

(4) Synthesis of 2-[4-(3-methyl-2-thienyl)]propionic acid

To 100 ml of ethanol were added 3.0 g (0.0103 mole) of 2-dimethylamino-2-[4-(3-methyl-2-thienyl)phenyl]propionic acid obtained in (3) and 1.5 g of palladium-carbon (10%). The mixture was subjected to atmospheric catalytic reduction at 60° to 70° C. After a theoretical quantity of hydrogen had been absorbed, the palladium-carbon was removed by filtration and the filtrate was freed from the solvent by distillation under reduced pressure to obtain 2.4 g (94.7% yield) of 2-[4-(3-methyl-2-thienyl)phenyl]propionic acid. A sample of the acid recrystallized from cyclohexane was mixed with a sample of the acid obtained in Example 1-(5). The mixture showed no mixed melting point depression.

EXAMPLE 5

(1) Synthesis of 2-[4-(3-methyl-2-thienyl)phenyl]propionaldehyde

To a stirred dispersion of 1.3 g (0.0535 mole) of magnesium turnings in 20 ml of anhydrous tetrahydrofuran was added dropwise 5.0 g of ethyl bromide to cause reaction and the mixture was then heated under reflux for 30 minutes. After completion of the reaction, the mixture was cooled to 0° C. To the mixture, while maintaining the temperature at 0° to 10° C., was added dropwise 5.0 g of chloromethyl ethyl ether, followed by adding a solution of 5.0 g (0.0232 mole) of 4-(3-methyl- 2-thienyl)acetophenone in 10 ml of anhydrous tetrahydrofuran. The mixture was then stirred at room temperature for 2 hours. The reaction mixture was poured into a solution of 5.0 g of ammonium chloride in 50 ml of water. After addition of 50 ml of diethyl ether, the ether layer was separated, dried over anhydrous magnesium sulfate and freed from the solvent by distillation under reduced pressure. The residue was admixed with 20 ml of acetic acid and heated under reflux for 4 hours, after which the solvent was removed by distillation under reduced pressure. The residue was purified by silica gel column chromatography (developing solvent: benzene/n-hexane=2/1) to obtain 2.5 g (47% yield) of 2-[4-(3-methyl-2-thienyl)phenyl]propionaldehyde.

(2) Synthesis of 2-[4-(3-methyl-2-thienyl)phenyl]propionic acid

In a manner similar to that in Example 1 - (5), 2-[4-(3-methyl-2-thienyl)phenyl]propionic acid was obtained from 2-[4-(3-methyl-2-thienyl)phenyl]propionaldehyde prepared in (1) above.

EXAMPLE 6

Synthesis of 2-[4-(3-methyl-2-thienyl)phenyl]propionic acid

To a mixture of 1.2 g (0.05 mole) of magnesium turnings and 50 ml of anhydrous tetrahydrofuran was added under a nitrogen stream one drop of ethyl bromide, followed by adding 10 g (0.0395 mole) of 4-(3-methyl-2-thienyl)-1-bromobenzene (boiling point 171°–175° C./16–17 mmHg). After refluxing for 30 minutes, the mixture was cooled. To the mixture was added a solution of 2.8 g (0.0205 mole) of anhydrous zinc chloride in 50 ml of anhydrous tetrahydrofuran, and the mixture was stirred at room temperature for 3 hours. To the mixture was added 7.2 g (0.0398 mole) of ethyl 2-bromopropionate. After having been stirred at 50° to 60° C. for one hour, the mixture was freed from the solvent by distillation under reduced pressure. The residue was mixed with 50 ml of 2 N hydrochloric acid and 50 ml of benzene. The organic layer was separated, washed with water, and freed from the solvent by distillation under reduced pressure. The residue was mixed with 50 ml of an ethanol solution containing 2.3 g of sodium hydroxide, heated under reflux for 3 hours, and then freed from the ethanol by distillation. The residue was mixed with 100 ml of water and 50 ml of benzene. The aqueous layer was separated, neutralized with hydrochloric acid, and the liberated oily substance was extracted with cyclohexane. The extract solution was dried over anhydrous magnesium sulfate and freed from the solvent by distillation under reduced pressure. The residue was purified by silica gel column chromatography (developing solvent: cyclohexane) to obtain 3.2 g (32.9% yield) of intended 2-[4-(3-methyl-2-thienyl)phenyl]propionic acid.

EXAMPLE 7

(1) Synthesis of 3-methyl-3-[4-(3-methyl-2-thienyl)phenyl]glycidonitrile

In 50 ml of xylene was dissolved 15 g (0.0694 mole) of 4-(3-methyl-2-thienyl)acetophenone, followed by adding 6.6 g (0.0874 mole) of chloroacetonitrile. To the solution cooled to −20° to −10° C. was added dropwise a sodium tert.-amylate solution (prepared by stirring 3.34 g of sodium amide and 7.5 g of tert.-amyl alcohol in 110 ml of xylene at 60° C. for 4 hours), while maintaining the temperature of the solution at −5° to 0° C. After completion of the addition, the mixture was stirred at the same temperature for one hour, then at room temperature for a further one hour, and mixed with 40 ml of water. After filtration of the reaction mixture, the organic layer was separated while the aqueous layer was mixed with 30 ml of xylene. The organic layer was separated from the aqueous layer and combined with the previously separated organic layer. The combined organic layer was dried over anhydrous magnesium sulfate and the solvent was removed by distillation under reduced pressure. The residue was purified by silica gel column chromatography (developing solvent: benzene/n-hexane=2/1) to obtain 6.9 g (39% yield) of oily 3-methyl-3-[4-(3-methyl-2-thienyl)phenyl]glycidonitrile.

I.R. (liquid film): $\nu_{CN}$ 2250 cm$^{-1}$.

NMR (CDCl$_3$): 60 MHz, internal standard TMS $\tau$ value: 8.10,

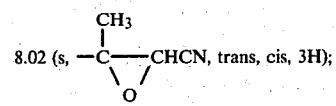

8.02 (s, trans, cis, 3H);

7.67 (s, CH$_3$ at 3-position of thiophene, 3H);

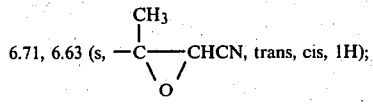

6.71, 6.63 (s, trans, cis, 1H);

3.10 (d, H at 4-position of thiophene, 1H, J=5 Hz); 2.82 (d, H at 5-position of thiophene, 1H, J=5 Hz); 2.25–2.91 (m, H at 2-, 3-, 5- and 6-positions of benzene, 4H)

(2) Synthesis of 2-acetoxy-3-methyl-3-[4-(3-methyl-2-thienyl)phenyl]acrylonitrile A 30-ml portion of the toluene solution containing 3.7 g (0.0145 mole) of 3-methyl-3-[4-(3-methyl-2-thienyl)phenyl]glycidonitrile obtained in (1) was saturated with dried hydrogen chloride and stirred for a further one hour so that 2-hydroxy-3-methyl-3-[4-(3-methyl-2-thienyl)phenyl]-3-chloropropionitrile may be formed. To the reaction mixture, which had been freed from the remaining hydrogen chloride by introducing dried nitrogen, was added 1.43 g (0.0181 mole) of pyridine and 1.70 g (0.0167 mole) of acetic anhydride, followed by adding 2.1 g (0.0207 mole) of triethylamine. After refluxing for 15 hours, the reaction mixture was washed with diluted hydrochloric acid, dried over anhydrous sodium sulfate, and freed from the solvent by distillation under reduced pressure to obtain 4.2 g (92% yield) of oily 2-acetoxy-3-methyl-3-[4-(3-methyl-2-thienyl)phenyl]acrylonitrile.

I.R. (liquid film): $\nu_{CN}$ 2230 cm$^{-1}$. $\nu_{C=O}$ 1770 cm$^{-1}$.

(3) Synthesis of 2-[4-(3-methyl-2-thienyl)phenyl]propionic acid

In 30 ml of toluene was dissolved 4.2 g (0.014 mole) of the 2-acetoxy-3-methyl-3-[4-(3-methyl-2-thienyl)phenyl]acrylonitrile obtained in (2), followed by the addition of 15 ml of methanol and 10 ml of a 30% aqueous sodium hydroxide solution. After refluxing with stirring for about 8 hours, the aqueous layer was separated and 20 ml of a 5% aqueous sodium hydroxide solution was added to the organic layer. The aqueous layer was separated and combined with the aqueous layer previously separated. The combined aqueous layer was acidified with about 10 ml of concentrated hydrochloric acid and extracted twice with 30-ml portions of ethyl acetate. The ethyl acetate solution was dried over anhydrous sodium sulfate and freed from the solvent by distillation under reduced pressure. The residue was crystallized by the addition of n-hexane to obtain 3.2 g (92% yield) of 2-[4-(3-methyl-2-thienyl)-phenyl]propionic acid.

EXAMPLE 8

(1) Synthesis of methyl 2-hydroxy-3-[4-(3-methyl-2-thienyl)phenyl]-3-butenoate

In 35 ml of toluene was dissolved 7.0 g (0.0243 mole) of the methyl 3-methyl-3-[4-(3-methyl-2-thienyl)phenyl]glycidate obtained in Example 1 - (2). To the solution was added at room temperature 0.45 ml of a dioxane solution containing 0.05 ml of concentrated sulfuric acid. After stirring for 30 minutes, the reaction mixture was washed with water, dried over anhydrous magnesium sulfate, and concentrated to obtain 7.0 g of oily methyl 2-hydroxy-3-[4-(3-methyl-2-thienyl)phenyl]3-butenoate.

I.R. (liquid film): $\nu_{OH}$ 3480 cm$^{-1}$. $\nu_{C=O}$ 1740 cm$^{-1}$.

(2) Synthesis of 2-[4-(3-methyl-2-thienyl)phenyl]propionic acid

In 14 ml of anhydrous methanol was dissolved 7.0 g (0.0243 mole) of the methyl 2-hydroxy-3-[4-(3-methyl-2-thienyl)phenyl]-3-butenoate obtained in (1). After addition of a methanol solution of sodium methylate prepared from 0.73 g (0.032 mole) of metallic sodium and 10 ml of anhydrous methanol, the mixture was stirred at room temperature for 2 hours. The mixture was then admixed with 20 ml of water, heated gradually, and refluxed for 30 minutes. After the reaction mixture had been cooled to room temperature, 4.2 ml of 30% aqueous hydrogen peroxide was slowly added thereto and the mixture was stirred at 40° to 50° C. for 1 hour. To the reaction mixture was added 30 ml of cyclohexane and the solution was adjusted to pH 3.0 with 6 N hydrochloric acid. The organic layer was separated, dried over anhydrous magnesium sulfate, and freed from the solvent by distillation under reduced pressure. The residue was purified by silica gel column chromatography (developing solvent: benzene/ethyl acetate=3/1) to obtain 3.3 g (55% yield) of crystalline 2-[4-(3-methyl-2-thienyl)phenyl]propionic acid. A sample of this acid recrystallized from cyclohexane was mixed with a sample obtained in Example 1 - (5). The mixture showed no depression of mixed melting point.

EXAMPLE 9

(1) Synthesis of 2-ethoxy-3-methyl-3-[4-(3-methyl-2-thienyl)phenyl]acrylonitrile In 30 ml of toluene was dissolved 2.55 g (0.010 mole) of the 3-methyl-3-[4-(3-methyl-2-thienyl)phenyl]glycidonitrile obtained in Example 7 - (1). The solution was saturated with dry hydrogen chloride and stirred for one hour, after which the remaining hydrogen chloride was driven off by introducing dried nitrogen. After addition of 0.50 g (0.013 mole) of sodium amide and 2.18 g (0.020 mole) of bromoethane, the mixture was stirred for 5 hours at room temperature, and then 1.5 g (0.015 mole) of triethylamine was added thereto, after which the mixture was refluxed for 5 hours. The reaction mixture was thoroughly shaken together with 100 ml of water and the organic layer was separated. The organic layer was dried over anhydrous sodium sulfate, and freed from the solvent by distillation under reduced pressure to obtain 2.4 g (85% yield) of oily 2-ethoxy-3-methyl-3-[4-(3-methyl-2-thienyl)phenyl]acrylonitrile.

I.R. (liquid film): $\nu_{C\equiv N}$ 2250 cm$^{-1}$.

(2) Synthesis of 3-methyl-3-[4-(3-methyl-2-thienyl)phenyl]-2-oxopropionitrile

In 30 ml of toluene was dissolved 2.4 g (0.0085 mole) of 2-ethoxy-3-methyl-3-[4-(3-methyl-2-thienyl)phenyl]acrylonitrile obtained in (1). After addition of 4 ml of concentrated hydrochloric acid and 4 ml of methanol, the mixture was stirred under reflux for 6 hours. After completion of the reaction, 50 ml of water was added to the reaction mixture and the organic layer was separated. The aqueous layer was mixed with 20 ml of toluene and again the organic layer was separated. The organic layers were combined, thoroughly washed with 50 ml of water, dried over anhydrous sodium sulfate, and freed from the solvent by distillation under reduced pressure to obtain 1.8 g (84% yield) of oily 3-methyl-3-[4-(3-methyl-2-thienyl)phenyl]-2-oxopropionitrile.

I.R. (liquid film): $\nu_{C\equiv N}$ 2210 cm$^{-1}$. $\nu_{C=O}$ 1755 cm$^{-1}$.

(3) Synthesis of 2-[4-(3-methyl-2-thienyl)phenyl]propionic acid

In 30 ml of toluene was dissolved 1.8 g (0.0072 mole) of 3-methyl-3-[4-(3-methyl-2-thienyl)phenyl]-2-oxopropionitrile obtained in (2). After additioin of 15 ml of methanol and 20 ml of 20% aqueous sodium hydroxide solution, the mixture was stirred under reflux for 7 hours. After completion of the reaction, the aqueous layer was separated and the organic layer was washed with 20 ml of a 5% aqueous sodium hydroxide solution. Both aqueous layers were combined, acidified with about 10 ml of concentrated hydrochloric acid, and extracted twice with 30-ml portions of ethyl acetate. The ethyl acetate extract solution was dried over anhydrous sodium sulfate, and freed from the solvent by distillation under reduced pressure. The residue was crystallized by adding n-hexane to obtain 1.0 g (57% yield) of 2-[4-(3-methyl-2-thienyl)phenyl]propionic acid.

EXAMPLE 10

(1) Synthesis of methyl [1-[4-(3-methyl-2-thienyl)phenyl]ethylidene]cyanoacetate:

In 50 ml of benzene were dissolved 4.32 g (0.020 mole) of 4-(3-methyl-2-thienyl)acetophenone, 2.26 g (0.0228 mole) of methyl cyanoacetate, 0.23 g (0.003 mole) of ammonium acetate, and 1.80 g (0.030 mole) of acetic acid. The mixture was heated under reflux with stirring, while removing the water formed by the reaction, as an azeotrope with benzene. After 4 hours, 0.23 g (0.003 mole) of ammonium acetate and 0.60 g (0.010 mole) of acetic acid were added again, and the mixture was futher heated for 6 hours. The reaction mixture was cooled, and 50 ml of water was added thereto, after which the mixture was shaken vigorously. The benzene layer was separated, dried over anhydrous sodium sulfate, and freed from the benzene by distillation under reduced pressure. The residue was treated by silica gel column chromatography using a benzene-hexane (2:1) mixture as eluent. The intended fraction was concentrated to obtain 5.00 g (84% yield) of methyl[1-[4-(3-methyl-2-thienyl)phenyl]ethylidene]cyanoacetate.

I.R. (liquid film): $\nu_{C\equiv N}$ 2250 cm$^{-1}$.

NMR (CDCl$_3$): 60 MHz; internal standard TMS $\tau$ value: 7.69 (s, CH$_3$ at 3-position of thiophene, 3H);

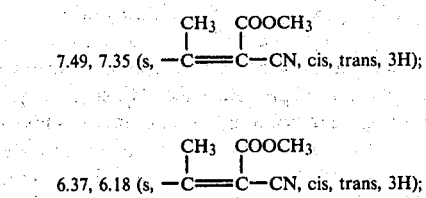

7.49, 7.35 (s, —C=C—CN, cis, trans, 3H);

6.37, 6.18 (s, —C=C—CN, cis, trans, 3H);

3.19 (d, H at 4-position of thiophene, 1H, J=5 Hz); 2.89 (d, H at 5-position of thiophene, 1H, J=5 Hz); 2.57 (s, H at 2-, 3-, 5- and 6-positions of benzene, 4H)

(2) Synthesis of 3-[4-(3-methyl-2-thienyl)phenyl]-2,3-epoxy-2-methoxycarbonylbutyramide In 20 ml of methanol were dissolved 5.00 g (0.0168 mole) of methyl[1-[4-(3-methyl-2-thienyl)phenyl]ethylidene]cyanoacetate and 1.68 g (0.0096 mole) of dipotassium hydrogenphosphate. To the mixture heated at 55° to 60° C. were added with vigorous stirring gradually over a period of one hour 7.25 ml (0.064 mole) of 30% aqueous hydrogen peroxide. After completion of the addition, the mixture was stirred for a further one hour at the same temperature. To the reaction mixture thus obtained were added 20 ml of water and 70 ml of benzene, and the mixture was shaken thoroughly. The benzene layer was separated, washed with 10 ml of a 10% aqueous sodium thiosulfate solution, dried over anhydrous sodium sulfate, and freed from the solvent by distillation under reduced pressure to obtain 4.98 g (89% yield) of 3-[4-(3-methyl-2-thienyl)phenyl]-2,3-epoxy-2-methoxycarbonylbutyramide.

I.R. $\nu_{C=O}$ 1750, 1680 cm$^{-1}$. $\nu_{NH}$ 3340, 3475 cm$^{-1}$.

(3) Synthesis of 3-[4-(3-methyl-2-thienyl)phenyl]-2-oxybutyramide

In 5 ml of methanol was dissolved 3.32 g (0.010 mole) of 3-[4-(3-methyl-2-thienyl)phenyl]-2,3-epoxy-2-methoxycarbonylbutyramide, followed by gradual addition of 15 ml (0.015 mole) of 1 N methanol solution of potassium hydroxide. The mixture was stirred at room temperature for one hour and freed from methanol by distillation under reduced pressure, and 40 ml of water was added thereto and 20 ml of benzene was then added to remove impurities, and the mixture was shaken thoroughly. The aqueous layer was separated, and 17 ml (0.017 mole) of 1 N hydrochloric acid was gradually added thereto, after which the mixture was heated with stirring to 90° C. to effect decarboxylation. After one hour of heating, the aqueous mixture was cooled and extracted with 70 ml of diethyl ether. The ether extract solution was dried over anhydrous magnesium sulfate and freed from diethyl ether by distillation under reduced pressure to obtain 2.10 g (77% yield) of 3-[4-(3-methyl-2-thienyl)phenyl]-2-oxobutyramide.

I.R.(KBr): $\nu_{C=O}$ 1650, 1705 cm$^{-1}$.

Melting point: 116°–117° C. (after recrystallization from n-hexane-benzene).

NMR (CDCl$_3$): 60 MHz; internal standard TMS $\tau$ value:

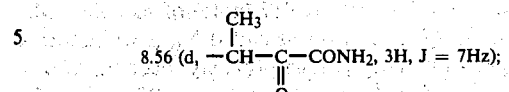

8.56 (d, —CH—C—CONH$_2$, 3H, J = 7Hz);

7.74 (s, CH$_3$ at 3-position of thiophene, 3H);

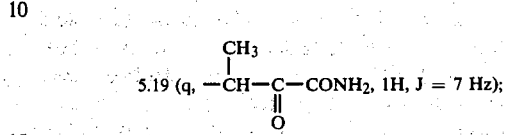

5.19 (q, —CH—C—CONH$_2$, 1H, J = 7 Hz);

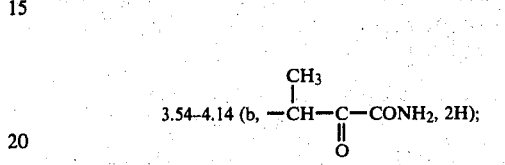

3.54–4.14 (b, —CH—C—CONH$_2$, 2H);

3.20 (d, H at 4-position of thiophene, 1H, J=5 Hz); 2.91 (d, H at 5-position of thiophene, 1H, J=5 Hz); 2.74 (s, H at 2-, 3-, 5- and 6-positions of benzene, 4H)

(4) Synthesis of 2-[4-(3-methyl-2-thienyl)phenyl]propionic acid

A solution of 2.00 g (0.0073 mole) of 3-[4-(3-methyl-2-thienyl)phenyl]-2-oxobutyramide in 10 ml of chloroform was added dropwise at 0° to 5° C. to an aqueous sodium hypobromite solution prepared from 36.5 ml (0.0365 mole) of 1 N aqueous sodium hydroxide solution and 1.5 g (0.0094 mole) of bromine. After completion of the addition, the mixture was stirred at 0° C. for 2 hours, then mixed with 20 ml of chloroform to remove impurities and shaken thoroughly. The aqueous layer was separated, mixed with 0.16 g (0.0015 mole) of sodium sulfite, and then with concentrated hydrochloric acid to adjust to pH 1–2. The aqueous layer was extracted with 50 ml of benzene and the benzene extract solution was dried over anhydrous magnesium sulfate, and freed from the benzene by distillation under reduced pressure. The residue was crystallized by addition of n-hexane to obtain 1.43 g (81% yield) of crude crystals of 2-[4-(3-methyl-2-thienyl)phenyl]propionic acid. Melting point 95°–96° C.

EXAMPLE 11

(1) Synthesis of diethyl[4-(3-methyl-2-thienyl)phenyl]malonate

To a solution of 1.4 g (0.06 mole) of metallic sodium in 50 ml of ethanol was added 10 g (0.038 mole) of ethyl 4-(3-methyl-2-thienyl)phenylacetate [I.R. (liquid film): $\nu_{C=O}$ 1735 cm$^{-1}$], followed by adding 14.3 g (0.121 mole) of diethyl carbonate. The mixture was stirred at 50° to 60° C. for 30 minutes and freed from the ethanol by distillation under reduced pressure. To the residue were added 15 ml of 1 N hydrochloric acid and 50 ml of benzene and the mixture was shaken thoroughly. The organic layer was dried over anhydrous magnesium sulfate and freed from the solvent by distillation under reduced pressure. The residue was purified by silica gel column chromatography (developing solvent: benzene/n-hexane=2/1) to obtain 7.8 g (58% yield) of oily diethyl [4-(3-methyl-2-thienyl)phenyl]malonate.

I.R.(liquid film): $\nu_{C=O}$ 1735 cm$^{-1}$.

(2) Synthesis of diethyl
α-methyl-α-[4-(3-methyl-2-thienyl)phenyl]malonate

To a solution of 0.40 g (0.017 mole) of metallic sodium in 25 ml of methanol was added 5 g (0.015 mole) of diethyl [4-(3-methyl-2-thienyl)phenyl]malonate obtained in (1). After 10 minutes, 6.7 g (0.047 mole) of methyl iodide was added to the above mixture and the mixture was stirred at room temperature for 2 hours. To the mixture were added 10 ml of 1 N hydrochloric acid and 30 ml of benzene and the mixture was shaken thoroughly. The organic layer was separated, dried over anhydrous magnesium sulfate, and freed from the solvent to obtain 4.3 g (83% yield) of diethyl α-methyl-α-[4-(3-methyl-2-thienyl)phenyl]malonate in oily form.

I.R.(liquid film): $\nu_{C=O}$ 1735 cm$^{-1}$.

(3) Synthesis of 2-[4-(3-methyl-2-thienyl)phenyl]propionic acid

To a solution of 1.4 g (0.035 mole) of sodium hydroxide in 30 ml of methanol was added 4 g (0.012 mole) of the diethyl α-methyl-α-[4-(3-methyl-2-thienyl)phenyl]malonate obtained in (2). The mixture was heated under reflux for one hour, and 20 ml of water and 20 ml of benzene were added thereto, after which the mixture was shaken thoroughly. The aqueous layer was separated and adjusted to pH 1. The liberated oily substance was extracted with diisopropyl ether and the extract solution was dried over anhydrous magnesium sulfate, treated with activated carbon, and freed from the solvent by distillation under reduced pressure. The residue was crystallized by adding n-hexane to obtain 2.4 g (85% yield) of 2-[4-(3-methyl-2-thienyl)phenyl]propionic acid.

EXAMPLE 12

(1) Synthesis of 2-(4-iodophenyl)propionaldehyde

In 143 ml of toluene were dissolved 47.7 g of 4-iodoacetophenone and 42.1 g of methyl monochloroacetate. While cooling at −10° to 0° C., 18.9 g of sodium methylate was added to the solution portionwise over a period of one hour. The mixture was stirred for one hour at 0° to 10° C., then for one hour at room temperature, and finally for one hour at 50° to 60° C. to allow the reaction to proceed. After completion of the reaction and cooling, 100 ml of water was added to the reaction mixture and the mixture was thoroughly shaken. The organic layer was separated and freed from the solvent by distillation under reduced pressure to obtain oily methyl 3-methyl-3-(4-iodophenyl)glycidate to which was added a solution of 10.8 g of sodium hydroxide in 14.3 ml of ethanol. The mixture was slowly heated and refluxed for 30 minutes. After cooling, the precipitated crystals were collected by filtration, and washed successively with ethanol and toluene. The crystals were then dispersed in 143 ml of toluene and heated to refluxing. To the dispersion was added dropwise 12.8 ml of glacial acetic acid and the refluxing was continued until no more evolution of carbon dioxide had been observed. The reaction mixture was cooled, washed with 100 ml of water, then with 50 ml of 0.1 N sodium hydroxide solution, freed from the solvent by distillation under reduced pressure, and then distilled (boiling point 153°–156° C./15 mmHg) to obtain 34 g of 2-(4-iodophenyl)propionaldehyde.

(2) Synthesis of 2-(4-iodophenyl)propionic acid

To a solution of 34 g of 2-(4-iodophenyl)propionaldehyde in 100 ml of ethylene chloride was added a solution of 16.5 g of sulfamic acid in 85 ml of water. To the mixture was added dropwise with stirring a solution of 15.2 g of sodium chlorite in 22 ml of water, while maintaining the temperature at 10° to 15° C. After stirring for 10 minutes, about 15 g of sodium hydrogensulfite was added in small portions to the mixture. The organic layer was separated, washed with water, and mixed with 150 ml of 1 N sodium hydroxide solution. The aqueous layer was separated and adjusted to pH 3.0 with 6 N hydrochloric acid to precipitate white crystals. The crystals were collected by filtration, washed with water, and dried to obtain 34 g (94% yield) of 2-(4-iodophenyl)propionic acid.

m.p. 101°–102° C. (after recrystallization from cyclohexane).

(3) Synthesis of 2-[4-(3-methyl-2-thienyl)phenyl]propionic acid

In 84 ml of anhydrous tetrahydrofuran, 27.8 g (0.157 mole) of 2-bromo-3-methyl-thiophene was reacted with 4.2 g (0.173 mole) of magnesium turnings to form a Grignard reagent.

To a solution of 34 g (0.123 mole) of 2-(4-iodophenyl)propionic acid in 125 ml of 1 N aqueous sodium hydroxide solution was added 9.2 g (0.0676 mole) of anhydrous zinc chloride to form zinc salt of said acid. The zinc salt was extracted with 100 ml of toluene and the extract solution was azeotropically dehydrated and then freed from the solvent by distillation under reduced pressure. To the residue was added 100 ml of tetrahydrofuran, followed by adding 0.035 g of palladium chloride. To the resulting mixture heated to 60° to 65° C. was added dropwise with stirring the Grignard reagent prepared above, to allow the reaction to proceed. After completion of the addition, the mixture was heated under reflux for 2 hours, then cooled, and freed from the solvent by distillation under reduced pressure. To the residue were added 100 ml of water, 12.5 ml of concentrated hydrochloric acid and 100 ml of toluene, with stirring. The organic layer was separated, washed several times with water, and mixed with 125 ml of 1 N aqueous sodium hydroxide solution to extract the alkali-soluble reaction products. The aqueous layer was separated, and 100 ml of cyclohexane was added thereto, after which the mixture was adjusted to pH 4 with 6 N hydrochloric acid while stirring. The organic layer was separated, washed with water, and dried over anhydrous magnesium sulfate. The magnesium sulfate was removed by filtration and the filtrate was continually stirred at 10° to 20° C. to precipitate crystals. The crystals were collected by filtration to obtain 26 g (95% yield) of 2-[4-(3-methyl-2-thienyl)phenyl]propionic acid.

Melting point: 98°–99° C. (recrystallized from a cyclohexane-ethanol mixture).

I.R. (KBr): $\nu_{C=O}$ 1700 cm$^{-1}$.

Elementary analysis for $C_{14}H_{14}O_2S$:

| | C% | H% |
| --- | --- | --- |
| Calcd.: | 68.27 | 5.73 |
| Found: | 68.15 | 5.73 |

(4) Synthesis of
d-2-[4-(3-methyl-2-thienyl)phenyl]propionic acid

In 24 ml of ethyl acetate was dissolved 6.00 g (24.4 mmol.) of dl-2-[4-(3-methyl-2-thienyl)phenyl]propionic acid, and 2.06 g (12.5 mmol.) of the methyl ester of D(−)-α-phenylglycine dissolved in 18 ml of ethyl acetate was dropped into the above solution with stirring over 90 min. The resulting suspension was stirred at said temperature for 30 min, and then cooled to 10° C. in 60 min, after which the suspension was stirred at 10° C. for 30 min. This suspension was filtered, and the crystals thus obtained were washed with 18 ml of ethyl acetate which had previously cooled. The crystals were dissolved in 40 ml of ethyl acetate at 65° C., and the resulting solution was gradually cooled to 10° C. to precipitate crystals. The crystals were collected by filtration, washed with cooled ethyl acetate, and thereafter dried at 50° C. to obtain 2.87 g of the D(−)-α-phenylglycine methyl ester salt of d-2-[4-(3-methyl-2-thienyl)phenyl]-propionic aicd.

In 30 ml of ethyl acetate was suspended 2.87 g of the above salt, 20 ml of 0.5 N hydrochloric acid was added to the suspension, and the suspension was stirred at 5° C. for 10 min. The resulting uniform ethyl acetate layer was washed with water and dried over anhydrous magnesium sulfate, after which the solvent was removed by distillation under reduced pressure. To the resulting oily residue were added 10 mg of seed crystals and 10 ml of n-hexane, and the resulting mixture was stirred to precipitate crystals, which were then collected by filtration to obtain 1.53 g of d-2-[4-(3-methyl-2-thienyl)-phenyl]propionic acid.

Melting point: 62°–63° C.
$[\alpha]_D^{20} = +51.3°$ (C=1.56, ethanol).

EXAMPLE 13

(1) Synthesis of 2-(4-iodophenyl)-2-methyloxirane

To a solution of 30 g of dimethyl sulfide in 30 ml of acetonitrile was added dropwise over a period of 30 minutes 30 g of dimethyl sulfate, while maintaining the temperature at 40° to 50° C., and the mixture was stirred for one hour at the same temperature. The reaction mixture was cooled to 25° C. and mixed with 30 g of 4-iodoacetophenone and 90 ml of acetonitrile. While stirring, 13.2 g of sodium methoxide was added to the mixture and stirring was continued for a further 30 minutes at room temperature to complete the reaction. Thereafter, the dimethyl sulfide and acetonitrile were removed by distillation, and to the residue were added 120 ml of cyclohexane and 120 ml of water, after which the mixture was thoroughly shaken. The organic layer was separated, dried over anhydrous magnesium sulfate, and freed from the solvent by distillation under reduced pressure to obtain 31.5 g (99% yield) of oily 2-(4-iodophenyl)-2-methyloxirane having a melting point of 44°–45° C.

(2) Synthesis of 2-(4-iodophenyl)propionaldehyde

To a solution of 15 g of 2-(4-iodophenyl)-2-methyloxirane in 75 ml of toluene was added 1.5 g of powdered Molecular Sieves 4A and the mixture was heated under reflux for 4 hours. After completion of the reaction, the Molecular Sieves was removed by filtration and the filtrate was concentrated and then distilled under reduced pressure to obtain 12.5 g (83% yield) of 2-(4-iodophenyl)propionaldehyde in oily form.

(3) Synthesis of 2-(4-iodophenyl)propionaldehyde dimethyl acetal

To a solution of 39.2 g of 2-(4-iodophenyl)propionaldehyde in 39.2 ml of methanol was added 0.2 g of p-toluenesulfonic acid, and the mixture was stirred for 10 minutes. After addition of 19.2 g of methyl orthoformate, stirring was continued for 30 minutes. After completion of the reaction, 1.0 g of sodium methylate was added to the reaction mixture and the solvent was removed by distillation under reduced pressure. On distillation of the residue, there was obtained 43.2 g of 2-(4-iodophenyl)propionaldehyde dimethyl acetal, b.p. 155°–160° C./15 mmHg.

(4) Synthesis of
2-[4-(3-methyl-2-thienyl)phenyl]propionaldehyde

In 84 ml of anhydrous tetrahydrofuran, 27.8 g (0.157 mole) of 2-bromo-3-methylthiophene was reacted with 4.2 g (0.173 mole) of magnesium turnings to form Grignard reagent.

In 122 ml of anhydrous tetrahydrofuran was dissolved 40.6 g (0.133 mole) of 2-(4-iodophenyl)propionaldehyde dimethyl acetal. After addition of 0.04 g of palladium chloride, the mixture was heated to 55° C. To the mixture was added dropwise the Grignard reagent prepared above, while maintaining the temperature at 55° to 60° C. After completion of the addition, the mixture was kept at the same temperature for one hour and the solvent was then removed by distillation under reduced pressure. To the residue were added 120 ml of cyclohexane, 80 ml of water and 5 ml of glacial acetic acid, and the mixture was thoroughly stirred. The organic layer was separated, washed with water, and concentrated. The concentrate was mixed with 250 ml of glacial acetic acid and allowed to react by heating under reflux for 4 hours. After completion of the reaction, the reaction mixture was freed from the solvent by distillation under reduced pressure to obtain 30 g (97% yield) of almost pure 2-[4-(3-methyl-2-thienyl)phenyl]-propionaldehyde in oily form.

(5) Synthesis of
2-[4-(3-methyl-2-thienyl)phenyl]propionic acid

In a manner similar to that in Example 1-(5), 2-[4-(3-methyl-2-thienyl)phenyl]propionic acid was obtained from 2-[4-(3-methyl-2-thienyl)phenyl]propionaldehyde.

EXAMPLE 14

(1) Synthesis of
2-[1-(4-iodophenyl)ethyl]-4,4-dimethyl-2-oxazoline

To a solution of 25 g of 2-(4-iodophenyl)propionic acid in 50 ml of chloroform was added 16.1 g of thionyl chloride and the mixture was heated under reflux for 2 hours. After completion of the reaction, the excess thionyl chloride and chloroform were removed by distillation under reduced pressure. The residue was dissolved in 50 ml of chloroform and added dropwise over a period of 30 minutes to a solution of 20 g of 2-amino-2-methyl-1-propanol in 50 ml of chloroform, while maintaining the temperature at 0° to 10° C. After completion of the dropwise addition, the mixture was stirred for 15 minutes and washed with 100 ml of water. To the chloroform layer, which had been dried over anhydrous magnesium sulfate, was added dropwise 17.7 g of phosphorus oxychloride at 10° to 20° C. to allow the reaction to proceed. After the dropwise addition, the mixture was stirred for one hour at room temperature. To the reaction mixture was added 100 ml of water, and than a 20% aqueous sodium hydroxide solution was added thereto with vigorous stirring to adjust the pH to 12, while maintaining the temperature at 10° to 20° C. The organic layer was separated, dried over anhydrous magnesium sulfate, and evaporated to dryness to obtain 30 g (96.5% yield) of 2-[1-(4-iodophenyl)ethyl]-4,4-dimethyl-2-oxazoline.

I.R.(KBr): $\nu_{C=N}$ 1645 cm$^{-1}$.

(2) Synthesis of 2-[1-[4-(3-methyl-2-thienyl)phenyl]ethyl]-4,4-dimethyl-2-oxazoline To a solution of 8.0 g of 2-[1-(4-iodophenyl)ethyl]-4,4-dimethyl-2-oxazoline in 24 ml of anhydrous tetrahydrofuran was added 0.080 g of palladium chloride and the mixture was kept at 60° to 65° C. On the other hand, a Grignard reagent was prepared from 5.2 g of 2-bromo-3-methylthiophene, 0.8 g of magnesium turnings and 15 ml of anhydrous tetrahydrofuran. The Grignard reagent was added dropwise to the above mixture over a period of 30 minutes, while maintaining the temperature at 60° to 65° C. After the addition, the mixture was stirred at the same temperature for one hour to complete the reaction. After removal of the solvent by distillation under reduced pressure, to the residual reaction mixture were added 50 ml of benzene, 50 ml of water and 5 ml of glacial acetic acid, and the mixture was shaken thoroughly. The organic layer was separated, washed with water, dried over anhydrous magnesium sulfate, and freed from the solvent by distillation under reduced pressure to obtain 6.8 g (93.3% yield) of oily 2-[1-[4-(3-methyl-2-thienyl)phenyl]ethyl]-4,4-dimethyl-2-oxazoline.

I.R.(liquid film): $\nu_{C=N}$ 1645 cm$^{-1}$.

(3) Synthesis of 2-[4-(3-methyl-2-thienyl)phenyl]propionic acid

In a mixture of 30 ml of glacial acetic acid, 6 ml of water and 2 ml of concentrated sulfuric acid was dissolved 6.0 g of 2-[1-[4-(3-methyl-2-thienyl)phenyl]ethyl]-4,4-dimethyl-2-oxazoline obtained in (2), and the mixture was heated under reflux for 4 hours. After completion of the reaction, to the reaction mixture were added 50 ml of water and 50 ml of benzene and the mixture was shaken thoroughly. The organic layer was separated, washed with water, and mixed with 25 ml of 1 N aqueous sodium hydroxide solution. After thorough shaking of the mixture, the aqueous layer was separated, and 20 ml of benzene was added thereto, after which 25 ml of 1 N hydrochloric acid was added thereto to neutralize the same. The organic layer was separated, washed with water, dried over anhydrous magnesium sulfate, and freed from the solvent by distillation under reduced pressure. The residue was crystallized by adding a small amount of n-hexane to obtain 4.0 g (82% yield) of 2-[4-(3-methyl-2-thienyl)phenyl]propionic acid.

EXAMPLE 15

(1) Synthesis of 2-(4-iodophenyl)propionaldehyde

In 143 ml of toluene were dissolved 47.7 g of 4-iodoacetophenone and 42.1 g of methyl monochloroacetate, and 18.9 g of sodium methylate was added portionwise over one hour while cooling to −10° to 0° C. While further stirring at 0° to 10° C. for one hour, at room temperature for one hour and then at 50° to 60° C. for one hour, the above solution was subjected to reaction. After the completion of the reaction, the solution was cooled to room temperature, and 100 ml of water was added thereto. The reaction mixture was thoroughly shaken, and the organic layer was separated, after which the solvent was removed from the organic layer by distillation under reduced pressure, to obtain oily methyl 3-methyl-3-(4-iodophenyl)glycidate. Thereto was added a solution of 10.8 g of sodium hydroxide in 143 ml of ethanol, and the resulting mixture was gradually heated and then refluxed for 30 min. The reaction mixture was then cooled to 10° to 15° C., and the crystals thus precipitated were collected by filtration and then washed with ethanol and toluene in this order. The crystals were suspended in 143 ml of toluene, and 12.8 ml of glacial acetic acid was added dropwise to the suspension while heating the suspension under reflux. The refluxing was continued until the generation of carbon dioxide gas was not observed. The reaction mixture was then cooled to room temperature, and washed with 100 ml of water and then with 50 ml of 0.1 N aqueous sodium hydroxide solution. The solvent was removed by distillation under reduced pressure and the residue was destilled under reduced pressure (153° to 156° C./15 mmHg) to obtain 34 g (yield 67.4%) of 2-(4-iodophenyl)propionaldehyde.

I.R. (liquid film): $\nu_{C=O}$ 1720 cm$^{-1}$. $\nu_{CH}$ 2710 cm$^{-1}$, 2805 cm$^{-1}$.

(2) Synthesis of 2-(4-iodophenyl)propionic acid

In 100 ml of ethylene chloride was dissolved 34 g of 2-(4-iodophenyl)propionaldehyde, and a solution of 16.5 g of sulfamic acid in 85 ml of water was added to the solution. A solution of 15.2 g of sodium chlorite in 22 ml of water was then dropped thereinto while keeping the solution at 10° to 15° C. The solution was stirred for 10 min, and 15 g of sodium hydrogen sulfite was added portionwise thereto. The organic layer was separated and then washed with water. To the organic layer was added 150 ml of 1 N aqueous sodium hydroxide solution, and the aqueous layer was then separated, after which the pH of the aqueous layer was adjusted to 3.0 with 6 N hydrochloric acid, upon which white crystals were precipitated. The crystals were collected by filtration, washed with water and then dried to obtain 34 g (yield 94%) of 2-(4-iodophenyl)propionic acid.

Melting point: 101°–102° C. (recrystallized from cyclohexane).

I.R. (KBr): $\nu_{C=O}$ 1685 cm$^{-1}$.

(3) Synthesis of d-2-(4-iodophenyl)propionic acid (i) In 90 ml of ethanol was dissolved 16.0 g (0.0544 mole) of cinchonidine by heating, and to the solution was added 30.0 g (0.109 mole) of 2-(4-iodophenyl)propionic acid, after which the resulting mixture was heated to form a solution, to which 390 ml of ethyl acetate was then added while heating the solution. The resulting solution was stirred for one hour at 60°±2° C. to precipitate crystals, and the resulting slurry was cooled gradually to room temperature. The crystals precipitated were collected by filtration to obtain 20.5 g of the cinchonidine salt of d-2-(4-iodophenyl)propionic acid. The resulting salt was suspended in ethyl acetate, stirred and then added to dilute hydrochloric acid. The resulting organic layer was thereafter separated, washed with water, and then dried over anhydrous magnesium sulfate, and thereafter concentrated to dryness to obtain 9.8 g (0.0355 mole) of d-2-(4-iodophenyl)-propionic acid of an optical purity of 90%. The crystals obtained were recrystallized from a mixed solvent of ethanol and cyclohexane to obtain 7.8 g (0.028 mole) of d-2-(4-iodophenyl)propionic acid.

Melting point: 138°–139° C.

$[\alpha]_D^{20} = +40.5°$ (C=2.82, ethanol).

(ii) In 75 ml of methanol was dissolved 30 g (0.109 mole) of 2-(4-iodophenyl)propionic acid, and thereto was added a half of a solution of 16.4 g (0.0558 mole) of cinchonidine in 165 ml of methanol at once at 60° C. Seed crystals were added to the solution to precipitate crystals, after which the remaining half of the solution of cinchonidine in methanol was added thereto at 60° C. over 30 min. The resulting mixture was stirred under reflux for one hour, and then cooled gradually to room temperature. The crystals thus precipitated were collected by filtration to obtain 27.6 g of the cinchonidine salt of d-2-(4-iodophenyl)propionic acid. The salt thus obtained was suspended in 150 ml of toluene, and the resulting suspension was stirred, after which 80 ml of 5% hydrochloric acid was added thereto. The resulting organic layer was separated, washed with 100 ml of water, and then dried over anhydrous magnesium sulfate, and thereafter concentrated to dryness to obtain 12.9 g (0.0467 mole) of d-2-(4-iodophenyl)propionic acid of an optical purity of 88%. The crystals obtained were recrystallized from a mixed solvent of cyclohexanone and ethanol to obtain 9.0 g (0.0326 mole) of d-2-(4-iodophenyl)propionic acid.

(4) Synthesis of d-2-[4-(3-methyl-2-thienyl)phenyl]propionic acid

In 28 ml of 1 N aqueous sodium hydroxide solution was dissolved 7.8 g (0.028 mole) of d-2-(4-iodophenyl)-propionic acid, and thereto was added 2.0 (0.015 mole) of anhydrous zinc chloride to form a zinc salt. To the resulting mixture was added 23.4 ml of toluene to extract the zinc salt, and the extract was subjected to azeotropic dehydration, and then to distillation under reduced pressure to remove the solvent, after which 23.4 ml of anhydrous tetrahydrofuran was added to the resulting residue.

On the other hand, 5.9 g (0.033 mole) of 2-bromo-3-methyl thiophene was reacted with 0.87 g of (0.036 mole) of magnesium turnings in 17.8 ml of anhydrous tetrahydrofuran to prepare a Grignard reagent.

To the solution of zinc d-2-(4-iodophenyl)propionate in anhydrous tetrahydrofuran obtained above was added 0.008 g of palladium chloride, and the resulting mixture was heated to 60° to 65° C., and the Grignard reagent prepared above was dropped into the mixture with stirring to effect reaction. After the whole amount of the Grignard reagent had been dropped, the reaction mixture was refluxed for 2 hours and then cooled to room temperature. After the cooling, the solvent was removed by distillation under reduced pressure, and 23.4 ml of water was added to the resulting residue, after which 3.0 ml of conc. hydrochloric acid and 23.4 ml of toluene were added thereto. The resulting mixture was stirred, and thereafter the organic layer was separated, which was washed with water several times. To the organic layer was added 28.0 ml of 1 N aqueous sodium hydroxide solution to extract the alkali-solubles with the sodium hydroxide solution. To the extract was added 23.4 ml of cyclohexane, and the pH of the solution was adjusted to 4 with 6 N hydrochloric acid, after which the organic layer was separated. This organic layer was washed with water, then dried over anhydrous magnesium sulfate and thereafter concentrated to obtain 6.2 g of an oily matter. To the oily matter was added 43 ml of hexane, and further a slight amount of d-2-[4-(3-methyl-2-thienyl)phenyl]propionic acid was added thereto, and the resulting mixture was stirred for 30 min. The resulting crystals were collected by filtration, to obtain 6.0 g (0.024 mole) of d-2-[4-(3-methyl-2-thienyl)phenyl]propionic acid.

Melting point: 62°–63° C. (recrystallized from a mixed solvent of cyclohexane and hexane).

I.R. (KBr): $\nu_{C=O}$ 1700 cm$^{-1}$.

$[\alpha]_D^{20} = +51.2°$ (C=2.01, ethanol).

What is claimed is:

1. 2-[4-(3-methyl-2-thienyl)phenyl]propionic acid represented by the formula,

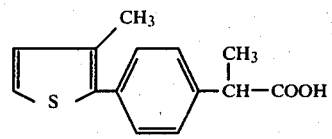

or a pharmaceutically acceptable salt thereof.

2. d-2-[4-(3-methyl-2-thienyl)phenyl]propionic acid or a pharmaceutically acceptable salt thereof.

3. dl-2-[4-(3-methyl-2-thienyl)phenyl]propionic acid or a pharmaceutically acceptable salt thereof.

4. A pharmaceutical composition containing a compound as claimed in claim 1, 2 or 3 as pharmaceutically active ingredient.

5. A pharmaceutical composition as claimed in claim 4, wherein the amount of the active ingredient per unit is 10 to 100 mg.

6. A method for alleviating the symptoms of inflammation and pain, which comprises administering to an animal suffering from such symptoms 0.1 to 50 mg/kg dialy of a compound as claimed in claim 1, 2 or 3.

7. The method according to claim 6, wherein the inflammation and the pain are caused by rheumatism.